United States Patent
Plavina et al.

(10) Patent No.: US 10,955,422 B2
(45) Date of Patent: Mar. 23, 2021

(54) METHOD OF ASSESSING RISK OF PML

(71) Applicant: Biogen MA Inc., Cambridge, MA (US)

(72) Inventors: Tatiana Plavina, North Reading, MA (US); John P. Carulli, Southborough, MA (US); Leonid Gorelik, Quincy, MA (US); Teresa Compton, Concord, MA (US)

(73) Assignee: Biogen MA, Inc., Cambridge, MA (US)

( * ) Notice: Subject to any disclaimer, the term of this patent is extended or adjusted under 35 U.S.C. 154(b) by 387 days.

(21) Appl. No.: 15/120,573

(22) PCT Filed: Feb. 27, 2015

(86) PCT No.: PCT/US2015/018069
§ 371 (c)(1),
(2) Date: Aug. 22, 2016

(87) PCT Pub. No.: WO2015/131078
PCT Pub. Date: Sep. 3, 2015

(65) Prior Publication Data
US 2017/0016919 A1 Jan. 19, 2017

Related U.S. Application Data

(60) Provisional application No. 61/945,778, filed on Feb. 27, 2014.

(51) Int. Cl.
*G01N 33/53* (2006.01)
*G01N 33/68* (2006.01)
*C12Q 1/6883* (2018.01)

(52) U.S. Cl.
CPC ....... *G01N 33/6896* (2013.01); *C12Q 1/6883* (2013.01); *C12Q 2600/118* (2013.01); *C12Q 2600/158* (2013.01); *G01N 2333/025* (2013.01); *G01N 2800/28* (2013.01); *G01N 2800/50* (2013.01)

(58) Field of Classification Search
CPC ......... G01N 33/6896; G01N 2333/025; G01N 2800/28; G01N 2800/50; C12Q 1/6883; C12Q 2600/118; C12Q 2600/158
See application file for complete search history.

(56) References Cited

U.S. PATENT DOCUMENTS

| 9,316,641 B2 | 4/2016 | Gorelik et al. |
| 2013/0022961 A1 | 1/2013 | Gorelik et al. |

FOREIGN PATENT DOCUMENTS

| WO | 2012166971 A2 | 12/2012 |
| WO | 2013057092 A1 | 4/2013 |

OTHER PUBLICATIONS

Handbook of Chemistry and Physics, 49th Edition, 1968, Weast (ed.), The Chemical Rubber Co., Cleveland, Ohio, p. A-245.*
Strausberg et al, in Microarrays and Cancer Research, 2002, Warrington et al (eds.), Eaton Publishing, Westborough, MA, pp. xi-xvi.*
Notterman et al, in Microarrays and Cancer Research, 2002, Warrington et al (eds.), Eaton Publishing, Westborough, MA, pp. 81-111.*
International Search Report and Written Opinion from corresponding International Application No. PCT/US2015/018069 dated Aug. 4, 2015.
Lindberg et al., "Natalizumab alters transcriptional expression profiles of blood cell subpopulations of multiple sclerosis patients", Journal of Neuroimmunology, Feb. 2008, vol. 194, No. (1-2), pp. 153-164, especially abstract, p. 161, Table 4.
Extended European Search report issued in European Application No. 15754919.7, dated Oct. 24, 2017.

* cited by examiner

*Primary Examiner* — James Martinell
(74) *Attorney, Agent, or Firm* — Todd A. Lorenz

(57) ABSTRACT

The invention relates to methods of assessing a patient's risk of developing Progressive Multifocal Leukoencephalopathy (PML).

27 Claims, 4 Drawing Sheets

METHOD OF ASSESSING RISK OF PML

CROSS-REFERENCE TO RELATED APPLICATIONS

This application is the U.S. National Phase Application under 35 U.S.C. § 371 of International Application No. PCT/US2015/018069, filed Feb. 27, 2015, which claims the benefit of U.S. Provisional Application No. 61/945,778, filed Feb. 27, 2014. The entire contents of the aforesaid applications are incorporated herein by reference.

FIELD OF THE INVENTION

The invention relates to methods of assessing a patient's risk of developing Progressive multifocal leukoencephalopathy (PML).

BACKGROUND OF INVENTION

The anti-VLA-4 (Very Late Antigen 4) antibody therapeutic natalizumab is indicated to treat relapsing forms of multiple sclerosis (MS) and moderate-to-severe Crohn's Disease. Natalizumab treatment, however, is associated with an increased risk of progressive multifocal leukoencephalopathy (PML), an opportunistic brain infection caused by the JC virus (JCV). PML occurs primarily in immunocompromised individuals and in patients receiving certain immunomodulatory therapies, including natalizumab. PML is hypothesized to be the result of a complex interaction between host and viral factors, leading to reactivation and mutation of latent archetype JCV to a neurotrophic form which can infect oligodendrocytes in the central nervous system.

SUMMARY OF INVENTION

The invention relates, inter alia, to assays for detecting the presence and/or amount of one or more B cell marker in a biological fluid, e.g., whole blood, serum or plasma, which can be used, e.g., to predict a risk of developing Progressive Multifocal Leukoencephalopathy (PML), and to various other methods, including methods of evaluating and/or treating patients. Also included are kits, reaction mixtures and arrays for predicting risk of developing PML.

Accordingly, in one aspect, the invention features, a method of evaluating a patient's risk of developing PML, the method comprising: determining expression levels of one or more B cell marker, e.g., one or more B cell marker described herein (e.g., one or more of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b) in a biological sample from the patient (e.g., a whole blood, serum or plasma sample), wherein if there is a significant difference in expression levels, e.g., compared to a reference standard (e.g., expression levels in a patient treated with an anti-VLA4 antibody, e.g., natalizumab, that does not develop PML), the patient is determined to be at higher risk of developing PML, and wherein if the expression levels are the same or substantially similar to the reference standard (e.g., expression levels in a patient treated with an anti-VLA4 antibody, e.g., natalizumab, that does not develop PML), the patient is determined to be at a lower risk of developing PML.

In some embodiments, the method further comprises obtaining a biological sample (e.g., a blood sample) from the patient. The sample can include a non-cellular fraction (e.g., plasma, serum, or other non-cellular body fluid). In one embodiment, the sample is a serum sample. In other embodiments, the biological sample is blood (e.g., whole blood). In certain embodiments, the blood can be further processed to obtain plasma or serum.

In some embodiments, the method further comprises obtaining (e.g., purifying or processing from the sample) a nucleic acid (e.g., genomic DNA, cDNA, RNA) or protein to determine expression levels of the B cell marker. Purification and/or processing of the sample can involve one or more of extraction, concentration, isolation, sorting, fixation, addition of reagents and the like. The processed or purified sample can contain compounds that are not naturally intermixed with the biological fluid in nature such as preservatives, anticoagulants, buffers, fixatives, nutrients, probes, labels, or the like.

In some embodiments, the B cell marker can be determined, e.g., using any suitable assay, e.g., an assay described herein including, e.g., an enzyme linked immunosorbant assay (ELISA), a radioimmunoassay (RIA), a Western blot or an immunohistochemical method. Alternatively, the level of B cell marker expression can be determined by the amount of nucleic acid (e.g., mRNA) in the biological sample. For example, B cell marker nucleic acids expression (e.g., mRNA levels) amounts can be readily determined using any suitable assay, e.g., an assay described herein including, e.g., Northern blotting, RT-PCR, or the use of biochips. In some embodiments, IgM expression levels are determined, e.g., IgM protein levels are determined, e.g., by a method described herein, and a decrease in IgM levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if IgM protein expression levels as determined are above a threshold amount (referred to as "a lower risk protein expression threshold level"). In one embodiment, the patient is determined to have a higher risk of PML if IgM protein levels as determined are below a threshold amount (referred to herein as "a higher risk protein expression threshold level"). In one embodiment, the patient is determined to have an intermediate risk of PML, e.g., the patient has IgM protein levels between the lower risk protein expression threshold level and the higher risk protein expression threshold level, and optionally, the patient is subjected to further evaluation of risk of PML, e.g., by other methods described herein. In one embodiment, the lower risk protein expression threshold level of IgM, e.g., as determined by a method described herein, is above 250 mg/dL. In one embodiment, the higher risk protein expression threshold level of IgM, e.g., as determined by a method described herein, is below 50 mg/dL. In one embodiment, the patient is determined to be at intermediate risk of developing PML if IgM protein levels are determined to be between 50 to 250 mg/dL, e.g., as determined by a method described herein. In some embodiments, a patient is identified as at higher risk of developing PML, if there is a 1.2, 1.3, 1.4, 1.5, 1.6, 1.7, 1.8, 1.9, 2 fold or more decrease in IgM expression levels as compared to the reference standard.

In some embodiments, IgM expression levels are determined, e.g., IgM nucleic acid levels are determined, e.g., by a method described herein, and a decrease in IgM nucleic acid levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if IgM nucleic acid levels as determined are above a threshold amount (referred to as "a lower risk nucleic acid threshold level"). In one embodiment, the patient is determined to have a higher risk of PML if IgM nucleic acid levels as determined are below a threshold amount (referred to herein as "a higher risk nucleic acid threshold level"). In one embodiment, the patient is determined to have an intermediate risk of PML, e.g., the patient has IgM nucleic acid levels between the lower risk nucleic acid threshold level and the higher risk nucleic acid threshold level, and optionally, the patient is subjected to further evaluation of risk of PML, e.g., by other methods described herein. In one embodiment, the lower risk nucleic acid threshold level for IgM, e.g., as determined by a method described herein, is above 4 log2 (e.g., 4.5 log2 or higher). In one embodiment, the higher risk nucleic acid threshold level of IgM, e.g., as determined by a method described herein, is 3 log2 or lower. In one embodiment, the patient is determined to be at intermediate risk of developing PML if IgM nucleic acid levels are determined to be between 3 log2 and 4.5 log2 (e.g., between 3 log2 and 4 log2), e.g., as determined by a method described herein. In some embodiments, a patient is identified as at higher risk of developing PML, if there is a 1.2, 1.3, 1.4, 1.5, 1.6, 1.7, 1.8, 1.9, 2 fold or more decrease in IgM nucleic acid levels as compared to the reference standard.

In some embodiments, the patient has not received treatment with an anti-VLA4 antibody, e.g., natalizumab, and prior to treatment with an anti-VLA4 antibody, e.g., natalizumab, IgM expression levels are determined, e.g., IgM protein levels and/or IgM nucleic acid levels are determined, e.g., by a method described herein, and compared to a reference standard (e.g., expression levels in a patient not yet treated with an anti-VLA antibody but that after being treated with an anti-VLA4 antibody, e.g., natalizumab, does not develop PML). If the IgM expression levels prior to treatment with an anti-VLA4 antibody are decreased as compared to the reference standard, this is indicative of a higher risk of the patient developing PML. In one embodiment, the patient is determined to be one of the following: being at lower risk of developing PML, e.g., based upon an IgM protein expression level that falls at or above a lower risk protein expression threshold level of IgM and/or based upon an IgM nucleic acid level that falls at or above a lower risk nucleic acid threshold level of IgM; being at higher risk of developing PML, e.g., based upon an IgM protein expression level that falls at or below a higher risk protein expression levels of IgM; and/or based upon an IgM nucleic acid level that falls at or below a higher risk nucleic acid threshold level of IgM or being at intermediate risk of developing PML, e.g., based upon an IgM protein expression level of IgM that falls between a lower risk protein expression threshold level and a higher risk protein expression threshold level for IgM and/or based upon an IgM nucleic acid level that falls between a lower risk nucleic acid threshold level of IgM and a higher risk nucleic acid threshold level of IgM. In one embodiment, the lower risk protein expression threshold level for IgM in patient that has not yet received treatment with an anti-VLA4 antibody, e.g., natalizumab, e.g., as determined by a method described herein, is above 200 mg/dL In one embodiment, the higher risk protein expression threshold level of IgM, e.g., as determined by a method described herein, is 100 mg/dL or lower. In one embodiment, the patient is determined to be at intermediate risk of developing PML if IgM protein expression levels are determined to be between 100 and 200 mg/dL, e.g., as determined by a method described herein.

In some embodiments, the IgM expression levels are IgM expression levels of IgM to a particular antigen, e.g., JCV or BKV. In some embodiments, the IgM expression levels are total IgM expression levels. In some embodiments, the IgM expression levels are a ratio, e.g., a ratio of IgM expression levels of IgM to a particular antigen, e.g., JCV or BKV, to total IgM expression levels.

In other embodiments, risk of PML is determined in a patient that is receiving an anti-VLA antibody, e.g., natalizumab, e.g., has been receiving administration of the anti-VLA antibody, e.g., natalizumab for at least one week, two weeks, one month, 2, 3, 4, 5, 6, 7, 8, 9, 10, 11 months, 1, 2 or 3 years at the time of determination.

In some embodiments, IgG1 expression levels are determined, e.g., IgG1 protein levels are determined, e.g., by a method described herein, and a decrease in IgG1 levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if IgG1 protein expression levels as determined are above a threshold amount (referred to as "a lower risk protein expression threshold level"). In one embodiment, the patient is determined to have a higher risk of PML if IgG1 protein levels as determined are below a threshold amount (referred to herein as "a higher risk protein expression threshold level"). In one embodiment, the patient is determined to have an intermediate risk of PML, e.g., the patient has IgG1 protein levels between the lower risk protein expression threshold level and the higher risk protein expression threshold level, and optionally, the patient is subjected to further evaluation of risk of PML, e.g., by other methods described herein. In one embodiment, the lower risk protein expression threshold level of IgG1, e.g., as determined by a method described herein, is above 1100 mg/dL. In one embodiment, the higher risk protein expression threshold level of IgG1, e.g., as determined by a method described herein, is below 240 mg/dL. In one embodiment, the patient is determined to be at intermediate risk of developing PML if IgG1 protein levels are determined to be between 240 to 1100 mg/dL, e.g., as determined by a method described herein. In some embodiments, a patient is identified as at higher risk of developing PML, if there is a 1.2, 1.3, 1.4, 1.5, 1.6, 1.7, 1.8, 1.9, 2 fold or more decrease in IgG1 expression levels as compared to the reference standard.

In some embodiments, IgG1 expression levels are determined, e.g., IgG1 nucleic acid levels are determined, e.g., by a method described herein, and a decrease in IgG1 nucleic acid levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if IgG1 nucleic acid levels as determined are above a threshold amount (referred to as "a lower risk nucleic acid threshold level"). In one embodiment, the patient is determined to have a higher risk of PML if IgG 1 nucleic acid levels as determined are below a threshold amount (referred to herein as "a higher risk nucleic acid threshold level"). In one embodiment, the patient is determined to have an intermediate risk of PML, e.g., the patient has IgG1 nucleic acid levels between the lower risk nucleic acid level and the higher risk nucleic acid level, and optionally, the patient is subjected to further evaluation of risk of PML, e.g., by other methods described herein. In some embodiments, a patient is identified as at higher risk of developing PML, if there is a 1.2, 1.3, 1.4, 1.5, 1.6, 1.7, 1.8, 1.9, 2 fold or more decrease in IgG1 nucleic acid levels as compared to the reference standard.

In some embodiments, the patient has not received treatment with an anti-VLA4 antibody, e.g., natalizumab, and prior to treatment with an anti-VLA4 antibody, e.g., natalizumab, IgG1 expression levels are determined, e.g., IgG1 protein levels and/or IgG1 nucleic acid levels are determined, e.g., by a method described herein, and compared to a reference standard (e.g., expression levels in a patient not yet treated with an anti-VLA antibody but that after being treated with an anti-VLA4 antibody, e.g., natalizumab, does not develop PML). If the IgG1 expression levels prior to treatment with an anti-VLA4 antibody are decreased as compared to the reference standard, this is indicative of a higher risk of the patient developing PML. In one embodiment, the patient is determined to be one of the following: being at lower risk of developing PML, e.g., based upon an IgG1 protein expression level that falls at or above a lower risk protein expression threshold level of IgG1 and/or based upon an IgG1 nucleic acid level that falls at or above a lower risk nucleic acid threshold level of IgG1; being at higher risk of developing PML, e.g., based upon an IgG1 protein expression level that falls at or below a higher risk protein expression threshold level of IgG1; and/or based upon an IgG1 nucleic acid level that falls at or below a higher risk nucleic acid threshold level of IgG1 or being at intermediate risk of developing PML, e.g., based upon an IgG1 protein expression level of IgG1 that falls between a lower risk protein expression threshold level and a higher risk protein expression threshold level for IgG1 and/or based upon an IgG1 nucleic acid level that falls between a lower risk nucleic acid threshold level of IgG1 and a higher risk nucleic acid threshold level of IgG1. In one embodiment, the lower risk protein expression threshold level for IgG1 in patient that has not yet received treatment with an anti-VLA4 antibody, e.g., natalizumab, e.g., as determined by a method described herein, is above 600 mg/dL In one embodiment, the higher risk protein expression threshold level of IgG1, e.g., as determined by a method described herein, is 400 mg/dL or lower. In one embodiment, the patient is determined to be at intermediate risk of developing PML if IgG1 protein expression levels are determined to be between 400 and 600 mg/dL, e.g., as determined by a method described herein.

In some embodiments, the IgG1 expression levels are IgG1 expression levels of IgG1 to a particular antigen, e.g., JCV or BKV. In some embodiments, the IgG1 expression levels are total IgG1 expression levels. In some embodiments, the IgG1 expression levels are a ratio, e.g., a ratio of IgG1 expression levels of IgG1 to a particular antigen, e.g., JCV or BKV, to total IgG1 expression levels.

In some embodiments, CD72 expression levels are determined, e.g., CD72 protein levels are determined, e.g., by a method described herein, and a decrease in CD72 levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if CD72 protein expression levels as determined are above a threshold amount (referred to as "a lower risk protein expression threshold level"). In one embodiment, the patient is determined to have a higher risk of PML if CD72 protein levels as determined are below a threshold amount (referred to herein as "a higher risk protein expression threshold level"). In one embodiment, the patient is determined to have an intermediate risk of PML, e.g., the patient has CD72 protein levels between the lower risk protein expression threshold level and the higher risk protein expression threshold level, and optionally, the patient is subjected to further evaluation of risk of PML, e.g., by other methods described herein. In some embodiments, a patient is identified as at higher risk of developing PML, if there is a 1.2, 1.3, 1.4, 1.5, 1.6, 1.7, 1.8, 1.9, 2 fold or more decrease in CD72 expression levels as compared to the reference standard.

In some embodiments, CD72 expression levels are determined, e.g., CD72 nucleic acid levels are determined, e.g., by a method described herein, and a decrease in CD72 nucleic acid levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if CD72 nucleic acid levels as determined are above a threshold amount (referred to as "a lower risk nucleic acid threshold level"). In one embodiment, the patient is determined to have a higher risk of PML if CD72 nucleic acid levels as determined are below a threshold amount (referred to herein as "a higher risk nucleic acid threshold level"). In one embodiment, the patient is determined to have an intermediate risk of PML, e.g., the patient has CD72 nucleic acid levels between the lower risk nucleic acid threshold level and the higher risk nucleic acid threshold level, and optionally, the patient is subjected to further evaluation of risk of PML, e.g., by other methods described herein. In one embodiment, the lower risk nucleic acid threshold level for CD72, e.g., as determined by a method described herein, is above 7 log2 (e.g., 7.5 log2 or higher). In one embodiment, the higher risk nucleic acid threshold level of CD72, e.g., as determined by a method described herein, is 3 log2 or lower. In one embodiment, the patient is determined to be at intermediate risk of developing PML if CD72 nucleic acid levels are determined to be between 6.5 log2 and 8 log2 (e.g., between 7 log2 and 8 log2), e.g., as determined by a method described herein. In some embodiments, a patient is identified as at higher risk of developing PML, if there is a 1.2, 1.3, 1.4, 1.5, 1.6, 1.7, 1.8, 1.9, 2 fold or more decrease in CD72 nucleic acid levels as compared to the reference standard.

In some embodiments, the patient has not received treatment with an anti-VLA4 antibody, e.g., natalizumab, and prior to treatment with an anti-VLA4 antibody, e.g., natalizumab, CD72 expression levels are determined, e.g., CD72 protein levels and/or CD72 nucleic acid levels are determined, e.g., by a method described herein, and compared to a reference standard (e.g., expression levels in a patient not yet treated with an anti-VLA antibody but that after being treated with an anti-VLA4 antibody, e.g., natalizumab, does not develop PML). If the CD72 expression levels prior to treatment with an anti-VLA4 antibody are decreased as compared to the reference standard, this is indicative of a higher risk of the patient developing PML. In one embodiment, the patient is determined to be one of the following: being at lower risk of developing PML, e.g., based upon an CD72 protein expression level that falls at or above a lower risk protein expression threshold level of CD72 and/or based upon an CD72 nucleic acid level that falls at or above a lower risk nucleic acid threshold level of CD72; being at higher risk of developing PML, e.g., based upon an CD72 protein expression level that falls at or below a higher risk protein expression threshold level of CD72; and/or based upon an CD72 nucleic acid level that falls at or below a higher risk nucleic acid threshold level of CD72; or being at intermediate risk of developing PML, e.g., based upon an CD72 protein expression level of CD72 that falls between a lower risk protein expression threshold level and a higher risk protein expression threshold level for CD72 and/or based upon an CD72 nucleic acid level that falls between a lower risk nucleic acid threshold level of CD72 and a higher risk nucleic acid threshold level of CD72.

In some embodiments, CD22 expression levels are determined, e.g., CD22 protein levels are determined, e.g., by a method described herein, and a decrease in CD22 levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if CD22 protein expression levels as determined are above a threshold amount (referred to as "a lower risk protein expression threshold level"). In one embodiment, the patient is determined to have a higher risk of PML if CD22 protein levels as determined are below a threshold amount (referred to herein as "a higher risk protein expression threshold level"). In one embodiment, the patient is determined to have an intermediate risk of PML, e.g., the patient has CD22 protein levels between the lower risk protein expression threshold level and the higher risk protein expression threshold level, and optionally, the patient is subjected to further evaluation of risk of PML, e.g., by other methods described herein. In some embodiments, a patient is identified as at higher risk of developing PML, if there is a 1.2, 1.3, 1.4, 1.5, 1.6, 1.7, 1.8, 1.9, 2 fold or more decrease in CD22 expression levels as compared to the reference standard.

In some embodiments, CD22 expression levels are determined, e.g., CD22 nucleic acid levels are determined, e.g., by a method described herein, and a decrease in CD22 nucleic acid levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if CD22 nucleic acid levels as determined are above a threshold amount (referred to as "a lower risk nucleic acid threshold level"). In one embodiment, the patient is determined to have a higher risk of PML if CD22 nucleic acid levels as determined are below a threshold amount (referred to herein as "a higher risk nucleic acid threshold level"). In one embodiment, the patient is determined to have an intermediate risk of PML, e.g., the patient has CD22 nucleic acid levels between the lower risk nucleic acid threshold level and the higher risk nucleic acid threshold level, and optionally, the patient is subjected to further evaluation of risk of PML, e.g., by other methods described herein. In one embodiment, the lower risk nucleic acid threshold level for CD22, e.g., as determined by a method described herein, is above 7 log2 (e.g., 7.5 log2 or higher). In one embodiment, the higher risk nucleic acid threshold level of CD22, e.g., as determined by a method described herein, is 6.5 log2 or lower. In one embodiment, the patient is determined to be at intermediate risk of developing PML if CD22 nucleic acid levels are determined to be between 6.5 log2 and 8 log2 (e.g., between 7 log2 and 8 log2), e.g., as determined by a method described herein. In some embodiments, a patient is identified as at higher risk of developing PML, if there is a 1.2, 1.3, 1.4, 1.5, 1.6, 1.7, 1.8, 1.9, 2 fold or more decrease in CD22 nucleic acid levels as compared to the reference standard.

In some embodiments, the patient has not received treatment with an anti-VLA4 antibody, e.g., natalizumab, and prior to treatment with an anti-VLA4 antibody, e.g., natalizumab, CD22 expression levels are determined, e.g., CD22 protein levels and/or CD22 nucleic acid levels are determined, e.g., by a method described herein, and compared to a reference standard (e.g., expression levels in a patient not yet treated with an anti-VLA antibody but that after being treated with an anti-VLA4 antibody, e.g., natalizumab, does not develop PML). If the CD22 expression levels prior to treatment with an anti-VLA4 antibody are decreased as compared to the reference standard, this is indicative of a higher risk of the patient developing PML. In one embodiment, the patient is determined to be one of the following: being at lower risk of developing PML, e.g., based upon a CD22 protein expression level that falls at or above a lower risk protein expression threshold level of CD22 and/or based upon a CD22 nucleic acid level that falls at or above a lower risk nucleic acid threshold level of CD22; being at higher risk of developing PML, e.g., based upon an CD22 protein expression level that falls at or below a higher risk protein expression threshold level of CD22; and/or based upon a CD22 nucleic acid level that falls at or below a higher risk nucleic acid threshold level of CD22 or being at intermediate risk of developing PML, e.g., based upon an CD22 protein expression level of CD22 that falls between a lower risk protein expression threshold level and a higher risk protein expression threshold level for CD22 and/or based upon a CD22 nucleic acid level that falls between a lower risk nucleic acid threshold level of CD22 and a higher risk nucleic acid threshold level of CD22.

In some embodiments, FcRLA expression levels are determined, e.g., FcRLA protein levels are determined, e.g., by a method described herein, and a decrease in FcRLA levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if FcRLA protein expression levels as determined are above a threshold amount (referred to as "a lower risk protein expression threshold level"). In one embodiment, the patient is determined to have a higher risk of PML if FcRLA protein levels as determined are below a threshold amount (referred to herein as "a higher risk protein expression threshold level"). In one embodiment, the patient is determined to have an intermediate risk of PML, e.g., the patient has FcRLA protein levels between the lower risk protein expression threshold level and the higher risk protein expression threshold level, and optionally, the patient is subjected to further evaluation of risk of PML, e.g., by other methods described herein. In some embodiments, a patient is identified as at higher risk of developing PML, if there is a 1.2, 1.3, 1.4, 1.5, 1.6, 1.7, 1.8, 1.9, 2 fold or more decrease in FcRLA expression levels as compared to the reference standard.

In some embodiments, FcRLA expression levels are determined, e.g., FcRLA nucleic acid levels are determined, e.g., by a method described herein, and a decrease in FcRLA nucleic acid levels as compared to a reference standard (e.g., expression levels in a patient treated with an anti-VLA4 antibody, e.g., natalizumab, that does not develop PML) is indicative of a higher risk of the patient developing PML. In one embodiment, the patient is determined to have a lower risk of PML if FcRLA nucleic acid levels as determined are above a threshold amount (referred to as "a lower risk nucleic acid threshold level"). In one embodiment, the patient is determined to have a higher risk of PML if FcRLA nucleic acid levels as determined are below a threshold amount (referred to herein as "a higher risk nucleic acid threshold level"). In one embodiment, the patient is determined to have an intermediate risk of PML, e.g., the patient has FcRLA nucleic acid levels between the lower risk nucleic acid threshold level and the higher risk nucleic acid threshold level, and optionally, the patient is subjected to further evaluation of risk of PML, e.g., by other methods described herein. In one embodiment, the lower risk nucleic acid threshold level for FcRLA, e.g., as determined by a method described herein, is above 7.5 log2 (e.g., 8 log2 or higher, e.g., 8.5 log2 or higher). In one embodiment, the higher risk nucleic acid threshold level of FcRLA, e.g., as determined by a method described herein, is 7.0 log2 or lower (e.g., 6.5 log2 or lower). In one embodiment, the patient is determined to be at intermediate risk of developing PML if FcRLA nucleic acid levels are determined to be between 7 log2 and 8.5 log2 (e.g., between 7.5 log2 and 8.5 log2), e.g., as determined by a method described herein. In some embodiments, a patient is identified as at higher risk of developing PML, if there is a 1.2, 1.3, 1.4, 1.5, 1.6, 1.7, 1.8, 1.9, 2 fold or more decrease in FcRLA nucleic acid levels as compared to the reference standard.

In some embodiments, the patient has not received treatment with an anti-VLA4 antibody, e.g., natalizumab, and prior to treatment with an anti-VLA4 antibody, e.g., natalizumab, FcRLA expression levels are determined, e.g., FcRLA protein levels and/or FcRLA nucleic acid levels are determined, e.g., by a method described herein, and compared to a reference standard (e.g., expression levels in a patient not yet treated with an anti-VLA antibody but that after being treated with an anti-VLA4 antibody, e.g., natalizumab, does not develop PML). If the FcRLA expression levels prior to treatment with an anti-VLA4 antibody are decreased as compared to the reference standard, this is indicative of a higher risk of the patient developing PML. In one embodiment, the patient is determined to be one of the following: being at lower risk of developing PML, e.g., based upon an FcRLA protein expression level that falls at or above a lower risk protein expression threshold level of FcRLA and/or based upon an FcRLA nucleic acid level that falls at or above a lower risk nucleic acid threshold level of FcRLA; being at higher risk of developing PML, e.g., based upon an FcRLA protein expression level that falls at or below a higher risk protein expression threshold level of FcRLA; and/or based upon an FcRLA nucleic acid level that falls at or below a higher risk nucleic acid threshold level of FcRLA; or being at intermediate risk of developing PML, e.g., based upon an FcRLA protein expression level of FcRLA that falls between a lower risk protein expression threshold level and a higher risk protein expression threshold level for FcRLA and/or based upon an FcRLA nucleic acid level that falls between a lower risk nucleic acid threshold level of FcRLA and a higher risk nucleic acid threshold level of FcRLA.

In one embodiment, the patient is determined to be at a higher risk of developing PML or intermediate risk of developing PML based upon expression levels of one or more B cell marker, and the patient is identified as someone who should receive additional testing to determine risk of developing PML.

In some embodiments, the method further comprises assessing (e.g., determining) a JC virus (JCV) antibody titer in a biological sample from the patient as a further indicator of risk (e.g., by a method described herein, and/or as described in WO 2011/085369 and WO2012/166971), e.g., wherein the patient has a negative prior immunosuppressant exposure classification; wherein if the titer is determined to be above a pre-determined level, e.g., above an index level of 0.7, 0.8, 0.9, 1.0, 1.1, 1.2, 1.3, 1.4, or 1.5, the patient is determined to be at a higher risk of developing PML, and wherein if the titer is determined to be at or below a pre-determined level, e.g., at or below an index level of 1.5, 1.4, 1.3, 1.2, 1.1, 1.0, 0.9, 0.8, or 0.7, the patient is determined to be at a lower risk of developing PML. In some embodiments, the pre-determined level is 0.9. In some embodiments, the pre-determined level is 1.2. In some embodiments, the pre-determined level is 1.5.

In some embodiments, the patient has been free of a non-anti-VLA-4 immunosuppressant therapy for a period within 1, 3, or 5 years. In some embodiments, the patient has been free of a non-anti-VLA-4 immunosuppressant therapy for the patient's lifetime, or since diagnosis with multiple sclerosis (e.g., relapsing, remitting multiple sclerosis).

In some embodiments, expression levels are determined for two, three, four, five, six, seven, eight, nine, ten, eleven, twelve, thirteen, fourteen, fifteen, sixteen, seventeen or eighteen B cell markers, e.g., expression levels are determined for two, three, four, five, six, seven, eight, nine, ten, eleven, twelve, thirteen, fourteen, fifteen, sixteen, seventeen or all of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b. In some embodiments, at least two B cell marker expression levels are determined, and the B cell markers include IgM, IgG1, CD72, CD22 and/or FcRLA. In some embodiments, at least two B cell marker expression levels are determined, and the B cell markers include CCL21, CXCL12 and/or CXCL13. In some embodiments, at least two B cell marker expression levels are determined, and the B cell markers include SIGLEC-3 and SIGLEC-9. In some embodiments, expression levels of at least two of: IgM and IgG1; IgM and CD72; IgM and CD22; IgM and FcRLA; IgG1 and CD72; IgG1 and CD22; IgG1 and FcRLA; CD72 and CD22; CD72 and FcRLA; CD22 and FcRLA, are determined.

In some embodiments, the patient has multiple sclerosis (e.g., relapsing, remitting multiple sclerosis).

In some embodiments, the patient has Crohn's disease (e.g., moderate to severely active Crohn's disease).

In some embodiments, the method further comprises assessing (e.g., determining) the expression level of VLA-4, e.g., VLA-4 protein and/or nucleic acid level, in a sample. In an embodiment, an expression level of VLA-4 in a specific subset of B cells present in a sample is determined. For example, in some embodiments, a VLA-4 expression level is determined in combination with an expression level of one or more B cell markers, e.g., one or more B cell markers disclosed herein.

In another aspect, the present invention provides a method of evaluating a patient's risk of developing PML, the method comprising: determining expression levels of one or more B cell marker, e.g., one or more B cell marker described herein (e.g., one or more of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b) (e.g., by a method described herein) in two or more biological samples, a first determination and a second or subsequent determination, (e.g., whole blood, plasma or serum samples) obtained from the patient over a period of time (e.g., 2, 3, 4, 5, 6, 7, 8, 9, 10, 11, 12, 13, 14, 15, 16, 17, 18, 19, 20, 21, 22, 23, 24 or more months) wherein the patient is administered an anti-VLA4 antibody during at least a portion of the period of time; and the patient's status of being at lower risk, intermediate risk or higher risk of developing PML is determined at the time of the initial determination and is reevaluated based upon the second or subsequent determination(s).

In various embodiments, the period of time is 6 months. In various embodiments, the period of time is 12 months. In various embodiments, the period of time is 18 months.

In certain embodiments, the two or more samples are consecutive samples. In some embodiments, the expression levels in every sample obtained from the patient over a period of time is determined to be at or above a lower risk expression threshold level. In some embodiments, the expression levels in every sample obtained from the patient over a period of time is determined to be between a lower risk expression threshold level and a higher risk expression threshold level. In some embodiments, expression levels of the initial determination are at or above a lower risk expression threshold level, and expression levels of a subsequent determination are between a lower risk expression threshold level and a higher risk expression threshold expression level or are at or below a higher risk expression threshold level. In some embodiments, the expression levels of an initial determination are between a lower risk expression threshold level and a higher risk expression threshold level, and the subsequent determination is at or above a lower risk expression threshold level, or at or below a higher risk expression threshold level.

In some embodiments, the patient has multiple sclerosis (e.g., relapsing, remitting multiple sclerosis).

In some embodiments, the patient has Crohn's disease (e.g., moderate to severely active Crohn's disease).

In one embodiment, the patient is determined to be at a higher risk of developing PML or intermediate risk of developing PML based upon expression levels of one or more B cell marker based upon the second or subsequent determination, and the patient is identified as someone who should receive additional testing to determine risk of developing PML, e.g., an additional risk or multiple risks described herein.

In some embodiments, if the patient is determined to be at lower risk of developing PML, then the patient is classified as being suitable for treatment with an anti-VLA4 therapy. In particular embodiments, the method further includes administering an anti-VLA4 therapy to the patient. In certain embodiments, the anti-VLA4 therapy is a natalizumab therapy. In some embodiments, the patient has previously received an anti-VLA4 therapy.

In some embodiments, the method further comprises providing information regarding the patient's classification, e.g., the patient's B cell expression levels, and, optionally, the patient's JCV titer and or anti-VLA4 antibody classification and/or immunosuppressant exposure classification to another party, e.g., a health care provider or reimbursement decider (e.g., an insurance or government agency).

In some embodiments, expression levels are determined for two, three, four, five, six, seven, eight, nine, ten, eleven, twelve, thirteen, fourteen, fifteen, sixteen, seventeen or eighteen B cell markers, e.g., expression levels are determined for two, three, four, five, six, seven, eight, nine, ten, eleven, twelve, thirteen, fourteen, fifteen, sixteen, seventeen or all of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b. In some embodiments, at least two B cell marker expression levels are determined, and the B cell markers include IgM, IgG1, CD72, CD22 and/or FcRLA. In some embodiments, at least two B cell marker expression levels are determined, and the B cell markers include CCL21, CXCL12 and/or CXCL13. In some embodiments, at least two B cell marker expression levels are determined, and the B cell markers include SIGLEC-3 and SIGLEC-9. In some embodiments, expression levels of at least two of: IgM and IgG1; IgM and CD72; IgM and CD22; IgM and FcRLA; IgG1 and CD72; IgG1 and CD22; IgG1 and FcRLA; CD72 and CD22; CD72 and FcRLA; CD22 and FcRLA, are determined.

In another aspect, the invention features, a kit for assessing risk of developing PML. In some embodiments, the kit can include probes for detecting the presence of a polypeptide or nucleic acid in a biological sample, e.g., a sample of whole blood, serum, or plasma. For example, the kit can comprise a labeled compound or agent capable of detecting a B cell marker or an mRNA encoding a B cell marker in a biological sample and means for determining the amount of the B cell marker or mRNA in the sample (e.g., an antibody which binds the B cell marker or an oligonucleotide probe which binds to DNA or mRNA encoding the B cell marker). In some embodiments, the kit further comprises instructions for interpreting the results obtained using the kit.

In some embodiments, the kit comprises plurality of probes for detecting a plurality of B cell markers.

In some embodiments, the kit can comprise one or more probes capable of identifying one or more B cell markers, e.g., one or more (2, 3, 4, 5, 6, 7, 8, 9, 10, 11, 12, 13, 14, 15, 16, 17 or all) B cell marker described herein (e.g., one or more of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b). In some embodiments, probes for two or more of IgM1, IgM1, IgG1, CD72 CD22 FCRLA can be included. In some embodiments, probes for two or more of CCL21, CXCL12 and/or CXCL13 can be included. In some embodiments, at least two probes for SIGLEC-3 and SIGLEC-9 can be included.

In some embodiments, the kit is for detection of a B cell marker polypeptide and the probe is selected from an antibody, antibody derivative, antibody fragment, and the like. For antibody-based kits, the kit can comprise, for example: (1) a first antibody (e.g., attached to a solid support) which binds to a B cell marker polypeptide, e.g., a B cell marker polypeptide described herein; and, optionally, (2) a second, different antibody which binds to either the polypeptide or the first antibody and is conjugated to a detectable label.

In some embodiments, the kit is for detection of a B cell marker nucleic acid and the kit comprises a probe selected from an oligonucleotide (labeled or non-labeled) fixed to a substrate, labeled oligonucleotide not bound with a substrate, pairs of PCR primers, molecular beacon probes, and the like. For oligonucleotide-based kits, the kit can comprise, for example: (1) an oligonucleotide, e.g., a detectably labeled oligonucleotide, which hybridizes to a nucleic acid sequence encoding a B cell marker polypeptide, e.g., a B cell marker described herein, or (2) a pair of primers useful for amplifying a nucleic acid molecule corresponding to a B cell marker. In some embodiments, the kit can further comprise one or more of, e.g., a buffering agent, a preservative, a protein stabilizing agent, and components necessary for detecting the detectable label (e.g., an enzyme or a substrate).

In some embodiments, the kit can further comprise a control sample or a series of control samples which can be assayed and compared to the test sample.

In some embodiments, the kit comprises a substrate, e.g., a plate with wells coated with an agent capable of binding to one or more B cell markers, e.g., one or more B cell markers described herein (e.g., one or more of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b). In one embodiment the substrate is coated with an agent capable of binding two or more of IgM, IgG1, CD72, CD22, FCRLA. In some embodiments, the substrate is coated with at least two agents capable of binding CCL21, CXCL12 and/or CXCL13. In some embodiments, the substrate is coated with at least two agents capable of binding SIGLEC-3 and SIGLEC-9. In some embodiments, the plate provided in a kit can be pre-coated with an agent capable of binding to one or more B cell markers.

In some embodiments, the kit comprises a substrate capable of binding to two or more B cell markers, e.g., two or more B cell markers described herein (e.g., one or more of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b). In one embodiment, the kit further comprises a B cell marker positive control. In one embodiment, the kit further comprises a B cell marker negative control.

In one embodiment, a kit comprises one or more reagents for detecting a complex containing B cell markers bound to a detection agent, for example, a detectable reagent, such as TMB (tetramethylbenzidine), a wash buffer, and a stop reagent.

In another aspect, the invention features, a substrate, e.g., a plate with wells, coated with an agent capable of binding to one or more B cell markers, e.g., one or more B cell markers described herein (e.g., one or more of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b). In some embodiments, the substrate, e.g., plate is coated with agents that detect two, three, four, five, six, seven, eight nine, ten, eleven, twelve, thirteen, fourteen, fifteen, sixteen, seventeen or all of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b. In one embodiment the substrate is coated with an agent capable of binding 2 or more of IgM, IgG1, CD72, CD22, FCRLA. In some embodiments, the substrate is coated with at least two agents capable of binding CCL21, CXCL12 and/or CXCL13. In some embodiments, the substrate is coated with at least two agents capable off binding SIGLEC-3 and SIGLEC-9.

The methods disclosed herein are based at least in part on the discovery that certain B cell marker expression levels can be indicators of a patient's risk of developing Progressive Multifocal Leukoencephalopathy (PML).

In another aspect, the invention features, a method of evaluating a patient's risk of developing PML, comprising acquiring knowledge of one or more B cell marker expression levels (e.g., one or more B cell marker provided in Table 4), e.g., as determined as described herein in a sample of the patient, and optionally comparing the acquired expression level with a reference standard disclosed herein, to thereby evaluate risk.

In one embodiment, inhibition cell expression levels are determined in a biological sample from a patient, such as a blood (whole blood, serum or plasma, or CSF or PBMC). If the expression level is significantly different from a reference standard (e.g., expression levels in a patient treated with an anti-VLA4 antibody, e.g., natalizumab, that does not develop PML), the patient is determined to be at higher risk of developing PML, and if the expression levels are the same or substantially similar to the reference standard (e.g., expression levels in a patient treated with an anti-VLA4 antibody, e.g., natalizumab, that does not develop PML), the patient is determined to be at a lower risk of developing PML. In some embodiments, the patient is determined to be at lower risk, intermediate risk or higher risk of PML (e.g., by the methods described herein).

In one embodiment, B cell marker expression levels are determined in more than one biological sample from a patient.

In one embodiment, the subject has multiple sclerosis, e.g., a multiple sclerosis patient that is already receiving therapy with an anti-VLA-4 antibody, e.g., natalizumab.

In one embodiment, the subject has Crohn's disease (e.g., moderate to severe Crohn's disease).

In one embodiment, the patient is determined to be at a lower risk of developing PML, and the patient is further administered an anti-VLA-4 therapy, such as an anti-VLA-4 antibody, such as natalizumab, or a fragment thereof (such as an antigen-binding fragment thereof).

In one embodiment, the patient is determined to be at a higher risk or intermediate risk of developing PML, and the patient is identified as someone who should receive an alternative therapy, e.g., the patient should stop receiving anti-VLA-4 antibody therapy, e.g., natalizumab, and, e.g., receive an alternative therapy, e.g., an alternative approved multiple sclerosis (MS) therapy such as Avonex®. In another embodiment, the patient is determined to be at a higher risk or intermediate risk of developing PML, and the patient is administered an anti-VLA-4 antibody therapy, e.g., natalizumab.

In one embodiment, the patient is determined to be at an intermediate risk or a higher risk of developing PML based upon the expression level of one or more B cell marker, and the patient is identified as someone who should receive additional testing to determine risk of developing PML, e.g., a risk identified herein.

In one embodiment, the patient is determined to have a lower risk of PML if B cell marker protein expression levels are at or above a lower risk protein expression threshold level (e.g., a lower risk protein expression threshold level described herein) and/or B cell marker nucleic acid levels are at or above a lower risk nucleic acid threshold level (e.g., a lower risk nucleic acid threshold level described herein). In one embodiment, the patient is determined to have a higher risk of PML if B cell marker protein levels as determined are at or below a higher risk protein expression threshold level (e.g., a higher risk protein expression threshold level described herein) and/or B cell marker nucleic acid levels are at or below a higher risk nucleic acid threshold level (e.g., a higher risk protein expression threshold level described herein). In one embodiment, the patient is determined to have an intermediate risk of PML, e.g., the patient has B cell marker protein levels between the lower risk protein expression threshold level and the higher risk protein expression threshold level and/or B cell marker nucleic acid levels are between a lower risk nucleic acid threshold level and a higher risk nucleic acid threshold level.

In one aspect, an entity, e.g., a healthcare provider, acquires information resulting from a B cell marker assay described herein, and responsive to the information, administers a treatment described herein to the patient, e.g., a MS patient.

In another aspect, a B cell marker assay described herein is performed on a patient, and then the patient is treated, e.g., the MS patient is treated, based on the results of the assay.

In any of the methods described herein, the B cell marker expression levels in a patient can be reevaluated at regular intervals, such as every 3 months, every 6 months, or every 12 months or at longer intervals or more frequently. An observed change, e.g., decrease, in one or more of the B cell marker expression levels can indicate an increase in the patient's risk of developing PML. For example, a decrease of 1 fold or 2 fold in B cell marker expression levels can indicate an increased risk of PML. A patient receiving an anti-VLA-4 therapy, such as a natalizumab, may stop therapy with the anti-VLA-4 therapy, and optionally begin therapy with an alternative agent, e.g., an immunosuppressant other than an anti-VLA-4 therapy, or other than natalizumab.

In one embodiment, a patient receiving an anti-VLA-4 antibody, e.g., natalizumab, can be monitored, e.g., every five, six, seven, eight, nine, ten, eleven, twelve, fifteen, twenty, thirty, forty months, for inhibition cell marker expression levels.

Evaluation of a patient as described herein can be conducted prior to administration of an anti-VLA-4 therapy, or after the patient has begun an anti-VLA-4 therapy.

In one embodiment, a patient is determined to be at a lower risk of PML, such as by an assay described herein, and the patient is administered an anti-VLA-4 therapy. In another embodiment, the patient is determined to be at a higher risk of PML and the patient is administered an anti-VLA-4 therapy, e.g., an anti-VLA-4 antibody, such as natalizumab. In yet another embodiment, the patient is determined to be at a higher risk of PML and the patient is administered a therapy other than an anti-VLA-4 therapy, such as an interferon, glatiramer acetate or a corticosteroid.

In one embodiment, the patient is determined to have an increased risk for PML, and the patient accordingly stops receiving an anti-VLA-4 therapy.

In one embodiment, after a patient is determined to be at a higher risk of PML, e.g., the patient is determined to have a B cell marker expression level that is below a higher risk threshold level (e.g., described herein), then the patient is not tested for expression levels of that B cell marker again. For example, the patient can stop therapy with an anti-VLA-4 therapy such as natalizumab, and not be tested again for expression levels of the B cell marker.

In one embodiment, a method of evaluating a patient as described herein, such as to determine B cell marker expression levels, can further include assessing other measures of other risk predictors. For example, a method of evaluating a patient can further include: (a) determining anti-JCV antibody titer or percent inhibition (b) determining if the patient has received extended treatment with an anti-VLA-4 therapy (e.g., longer than 24 months); or (c) determining if the patient has received a specified non-anti-VLA-4 immunosuppressant therapy (e.g., mitoxantrone or other therapies in the last 2, 3, 5 years or ever in the patient's life).

In one embodiment, the patient previously received an anti-VLA-4 therapy, e.g., natalizumab, and in another embodiment, the patient is administered an anti-VLA-4 therapy, based on an evaluation, e.g., an evaluation of B cell marker expression levels. For example, as a result of the evaluation, the patient can be classified as a candidate for anti-VLA-4 therapy. In one embodiment, a patient classified as a candidate for anti-VLA-4 therapy is further administered the therapy.

In another aspect, the invention features, a method of evaluating a patient, e.g., as a candidate to receive treatment with an anti-VLA-4 therapy.

The method includes, for example, acquiring or determining expression levels of one or more B cell marker (e.g., one or more B cell marker provided in Table 4) in a biological sample from the patient, e.g., by a method described herein. If the B cell marker expression level is determined to be above a higher risk threshold level, then the patient can be classified as being suitable for treatment with a first category of therapy, such as an anti-VLA-4 therapy, e.g., natalizumab. If the B cell marker expression level is determined to be at or below a higher risk threshold level, the patient is classified as being suitable for a second category of therapy, e.g., interferon, glatiramer acetate or a corticosteroid. Acquiring a B cell marker expression level in a sample of a patient may include removing a biological sample from the patient's body or analyzing a sample from the patient. The method of evaluation may also include administering a therapy, such as from the first category (e.g., natalizumab) or the second category (e.g., interferon, glatiramer acetate or a corticosteroid), to the patient.

As discussed above, methods of evaluating a patient can incorporate more than one consideration or factor. Thus, methods of evaluating a patient can further include:

(aa) determining anti-JCV antibody titer or percent inhibition.

(bb) determining if the patient has received extended treatment with an anti-VLA-4 therapy (e.g., longer than 24 months) and in embodiments providing a prior anti-VLA-4 therapy exposure classification; or (cc) determining if the patient has received a specified non-anti-VLA-4 immunosuppressant therapy (e.g., in the last 2, 3, 5 years or ever in the patient's life), and in embodiments providing a prior immunosuppressive exposure classification.

In one embodiment, the patient has previously received an anti-VLA-4 therapy. In another embodiment, the method includes administering an anti-VLA-4 therapy, e.g., natalizumab to the patient.

In one embodiment, the patient is classified as a candidate for anti-VLA-4 therapy, and the patient is further administered the anti-VLA-4 therapy.

Patients who have B cell marker expression levels at or above a higher risk threshold level, who have received an anti-VLA-4 therapy, such as natalizumab for 24 months or less, who have not previously received an immunosuppressant therapy (other than anti-VLA-4 therapy), and who test negative for exposure to JCV (e.g., negative for JCV antibodies) typically have the lowest risk for developing PML. Conversely, patients have B cell marker expression levels at or below a higher risk threshold level, who received anti-VLA-4 therapy for longer than 24 months, who have previously received an immunosuppressant therapy (other than an anti-VLA-4 therapy), and who test positive for exposure to JCV (e.g., positive for JCV antibodies) typically have the highest risk for developing PML. In one embodiment, if the patient has a B cell marker expression level at or above a higher risk expression threshold level, the patient is administered an anti-VLA4 therapy, e.g., an anti-VLA4 antibody, e.g., natalizumab. In one embodiment, if the if the patient has a B cell marker expression level at or above a higher risk expression threshold level and if the patient has a B cell marker expression level at or above a higher risk expression threshold level, the patient is administered an anti-VLA4 therapy, e.g., an anti-VLA4 antibody, e.g., natalizumab. In one embodiment, if the patient has a B cell marker expression level at or above a higher risk expression threshold level, has a positive JCV status and a positive prior immunosuppressant exposure classification that corresponds to having received a non-anti-VLA-4 immunosuppressant therapy within a preselected time period, e.g., within 1, 3, or 5 years, or in the patient's lifetime; and/or a negative prior immunosuppressant exposure classification that corresponds to being free of a non-anti-VLA-4 immunosuppressant therapy, the patient is administered an anti-VLA4 therapy, e.g., an anti-VLA4 antibody, e.g., natalizumab.

A patient's risk level for PML can be assessed by evaluating one, or any two, or any three or all four of the identified risk factors.

Enhanced monitoring can also include MRI scans to identify brain lesions due to PML.

In one embodiment, the patient has previously received an anti-VLA-4 therapy, and in another embodiment, the patient has not previously received an anti-VLA-4 therapy.

In yet another embodiment, the patient is classified as a candidate for anti-VLA-4 therapy, and an anti-VLA-4 therapy, e.g., natalizumab, is administered to the patient.

In one embodiment, making a determination, e.g., determining a patient's B cell marker expression levels, requires providing (e.g., obtaining or receiving) a biological sample from the patient, and performing an immunoassay, such as an assay described herein to detect the B cell marker protein expression levels in the sample. In another embodiment, a determination, e.g., determining a patient's B cell marker expression levels requires providing a biological sample from the patient and performing an assay, such as a PCR-based assay, to detect B cell marker nucleic acid in the sample.

If the patient is classified as a candidate for anti-VLA-4 therapy, the patient can be further administered an anti-VLA-4 therapy. A patient classified as a candidate for anti-VLA-4 therapy is determined to have a lower risk for developing PML.

A patient not classified as a candidate for anti-VLA-4 therapy, or determined to be a candidate for anti-VLA-4 therapy with enhanced monitoring for development of PML, is determined to have a higher risk for developing PML.

In an embodiment, a prior immunosuppressant exposure classification, if selected, is one of the following:

a positive prior immunosuppressant exposure classification that corresponds to having received a non-anti-VLA-4 immunosuppressant therapy within a preselected time period, e.g., within 1, 3, or 5 years, or in the patient's lifetime; and a negative prior immunosuppressant exposure classification that corresponds to being free of a non-anti-VLA-4 immunosuppressant therapy for a preselected time period, e.g., within 1, 3, or 5 years, or in the patient's lifetime.

In an embodiment, a prior VLA-4 therapy exposure classification, if selected, is one of the following:

a positive prior VLA-4 therapy exposure classification that corresponds to having received an anti-VLA-4 therapy for more than a preselected period of time, e.g., as much or more than 1, 2, 3, or 5 years; and a negative prior VLA-4 therapy exposure classification that corresponds to having received an anti-VLA-4 therapy for less than a preselected period of time, e.g., less than 6 months, 1, 2, 3, or 5 years.

In an embodiment, the method comprises providing a treatment suitability classification, which, e.g., can be selected from one of:

a positive treatment suitability classification that is correlated with suitability of the patient for anti-VLA-4 treatment (the positive treatment suitability classification can be further subdivided into positive treatment suitability classifications that are accompanied by various warnings or requirements for monitoring, such as increased monitoring for development of PML); and a negative treatment suitability classification that is correlated with unsuitability of the patient for anti-VLA-4 treatment, or suitability of the patient for anti-VLA-4 treatment, accompanied by various warnings or requirements for increased monitoring, such for development of PML.

A positive treatment suitability classification correlates with a lower risk of developing PML, and a negative treatment suitability classification correlates with a higher risk of developing PML. A lower risk of developing PML typically corresponds to a risk less than 0.2/1000 patients, and a higher risk of developing PML corresponds to a risk of ≥0.37/1000.

In an embodiment, if the patient is positive, e.g., has an expression level above a higher risk threshold level, for one or more B cell makers, e.g., one or more B cell markers described herein, the patient is assigned a positive treatment suitability classification. In some embodiments, if the patient is assigned an intermediate risk classification, the patient is assigned a positive treatment suitability classification, e.g., a modified positive treatment suitability classification that advises or requires monitoring for development of PML.

In one embodiment, the patient is assigned a positive treatment suitability classification, and the patient is further administered an anti-VLA-4 therapy, e.g., natalizumab.

In one aspect, a method of evaluating a patient, e.g., evaluating a patient's risk of developing PML, is also provided. The method includes two or more of (e.g., 3 or all of):

(aaa) determining whether the level of expression of a B cell marker (e.g., a B cell marker provided in Table 4) is less than or greater than a preselected criterion, e.g., as determined by a method disclosed herein;

(bbb) determining if the patient is negative or positive for JCV, such as by determining whether the level of anti-JCV antibodies is less than or greater than a preselected criterion, e.g., as determined by a method disclosed herein;

(ccc) determining if the patient has received an anti-VLA-4 therapy for greater than a preselected period of time (e.g., longer than 24 months), or less than a preselected period of time, e.g., 24 months or less, or has not received anti-VLA-4 therapy in a preselected period, e.g., in the last 2, 3, 5 years, or ever in the patient's life;

(ddd) determining if the patient has been free of a non-anti-VLA-4 immunosuppressant therapy for a preselected period of time or has received a non-anti-VLA-4 immunosuppressant therapy for a preselected period of time (a specified time) (e.g., the last 1, 2, 3, 4, 5, or 10 years, or ever in the patient's life); and responsive to the determinations, evaluating the patient.

In some embodiments, the method further requires administering a therapy to the patient. The therapy can, e.g., in the case of a lower risk or intermediate risk patient, be an anti-VLA-4 therapy (e.g., anti-VLA-4 antibody), or, e.g., in the case of a higher risk or intermediate risk patient, an alternative (non-anti-VLA-4) therapy, e.g., an interferon, glatiramer acetate or a corticosteroid.

In one aspect, a method of complying with instructions is provided. The instructions may, for example, appear on a government required package insert, e.g., an FDA (Food and Drug Administration) or EMA (European Medicines Agency) mandated package, and provide guidance for the use of an anti-VLA-4 therapy. The method of complying with instructions includes, optionally receiving the instructions; acquiring the results of an evaluative method described herein, and responsive to the acquired result, providing a recommendation for therapy to a patient, and optionally, further administering a therapy to the patient. The instruction can specify an evaluative method as described herein is essential for safely administering the therapy. The therapy may be an anti-VLA-4 therapy, e.g., natalizumab.

A method of evaluating a patient is provided, where the method requires providing a kit for the collection or transport of a patient sample to a healthcare provider; receiving a patient sample from the healthcare provider; performing a method as claimed herein.

A method of treating a patient is also provided. The method requires acquiring the result of a patient or sample evaluation method described herein, and responsive to the acquired result, administering a therapy to the patient. The therapy can be an anti-VLA-4 therapy, such as natalizumab.

A computerized method of authorizing reimbursement, such as for the cost of an anti-VLA-4 therapy, is also provided. The party to be reimbursed may be a third party payor, such as an insurance company or governmental agency. The method can include (a) acquiring the result of a patient evaluation method described herein, and recording the result on a computer readable medium; (b) acquiring evidence of administration of an anti-VLA-4 therapy to the patient and recording the evidence on a computer readable medium; and (c) if the result is consistent with administration of the anti-VLA-4 therapy, authorizing reimbursement to, or reimbursing, the party.

In one aspect, a method is provided for selecting or classifying a patient as a candidate to receive treatment with an anti-VLA-4 therapy, e.g., natalizumab. For example, the method can include determining that a patient has previously received an anti-VLA-4 therapy for 24 months or less, e.g., for 1 to 24 months, 2 to 20 months, 5 to 15 months, or 10 to 12 months, or that a patient has not previously received treatment with an immunosuppressant, and assessing expression levels of one or more B cell marker (e.g., one or more B cell marker provided in Table 4), e.g., by a method described herein. In one embodiment, assessing involves analyzing a sample from the patient. The sample can be, for example, a sample of blood, plasma, or serum, a sample of CSF, or a sample of PBMC. If the assessment indicates that the patient has a B cell marker expression level at or below a higher risk threshold level, then the patient is not selected or classified as a candidate for treatment with the anti-VLA-4 therapy. If the assessment indicates that the patient has a B cell marker expression levels above a higher risk threshold level, then the patient is selected or classified as a candidate to receive treatment with the anti-VLA-4 therapy.

An assay for B cell marker protein expression can be an immunoassay, such as an ELISA assay or other assay described herein. An assay for B cell marker nucleic acid can be, e.g., a PCR assay or a Next Generation Sequencing (NGS) method or any other method described herein.

A patient determined to be at lower risk or intermediate risk for PML can further be administered an anti-VLA-4 therapy, such as natalizumab. A patient determined to be at higher risk for PML can further be administered an alternative to an anti-VLA-4 therapy, such as an interferon, glatiramer acetate, a corticosteroid or a TNF agonist. In one embodiment, a patient determined to be at higher risk for PML can be further administered an anti-VLA-4 therapy, and can be required to receive an increased frequency of testing for PML, e.g., any risk described herein, e.g., by any method described herein, and where the patient is initially determined to have a B cell marker expression level below a lower risk threshold level, and is optionally JCV negative, or any other risk factor described herein, or has any combination of risk factors described herein, can also be required to received an increased frequency of testing for B cell marker levels and optionally, JCV levels, or any other risk factor described herein, or any combination of risk factors described herein.

In another aspect, a method of treating a patient is provided. The treatment method includes determining a patient's expression levels of one or more B cell marker, e.g., one or more B cell marker described herein (e.g., one or more of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b). Optionally, the method further includes determining the patient's status for JCV and/or determining the patient's prior exposure to an anti-VLA-4 therapy, and/or determining whether the patient previously received treatment with an immunosuppressant.

In some embodiments, if the patient is determined to have a B cell expression level at or below a higher risk threshold level, and optionally is determined to have received the anti-VLA-4 therapy for 24 months or less, is JCV negative, and not to have previously received treatment with an immunosuppressant, then the patient is determined to be at lower risk for PML, and the patient is administered the anti-VLA-4 therapy. If the patient is determined to have a B cell expression level at or below a higher risk threshold level, and optionally is determined to be JCV negative, to have received natalizumab for longer than 24 months (e.g., 25 months or longer), and not to have previously received treatment with an immunosuppressant, then the patient is determined to be at higher risk for PML, and the patient is administered an alternative to anti-VLA-4 therapy, e.g., an interferon, a corticosteroid, a statin or a TNF antagonist.

Determining the patient's prior exposure to an anti-VLA-4 therapy or an immunosuppressant can include asking the patient or a caregiver, e.g., a physician, nurse, parent or other caregiver. In some cases, determining the patient's prior exposure can include accessing the information in a database, e.g., a database of medical records.

Also provided is a method of determining a patient's risk for PML. The method includes determining expression levels of one or more B cell markers, e.g., one or more B cell markers described herein (e.g., one or more of IGHM, CD22, CD72, FCRLA, FCRL3, IGHD, IGKC, CCL21, CXCL12, CXCL13, BCMA, IgM, IgG, FCGR2A/B, SIGLEC-3, SIGLEC-9, IGFBP7, Notch1, Jag1 and C3b). In some embodiments, the method further includes determining the patient's previous exposure to an anti-VLA-4 therapy, and determining whether the patient previously received treatment with an immunosuppressant. Optionally, the patient's anti-JCV antibody status may also be determined. If the patient is determined to have received an anti-VLA-4 therapy for 24 months or less, and not to have previously received treatment with an immunosuppressant, then the patient is determined to be at lower risk for PML. If the patient is determined to have received anti-VLA-4 therapy for longer than 24 months, and not to have previously received treatment with an immunosuppressant, then the patient is determined to be at higher risk for PML. A patient determined to be at lower risk for PML may further be administered an anti-VLA-4 therapy, e.g., natalizumab. Conversely, a patient determined to be at higher risk for PML may further be administered an alternative to anti-VLA-4 therapy, e.g., an interferon, a corticosteroid, a statin or a TNF antagonist.

In an embodiment, the patient's B cell marker status is determined, and if the patient is determined to have a B cell marker expression level above a higher risk threshold level, e.g., one or more B cell markers disclosed herein, then the patient is determined to be at a lower risk of PML than if the patient was determined to have a B cell marker expression level at or below the higher risk threshold level.

In one embodiment, based on the determined risk for PML, e.g., based on the results of an assay described herein, e.g., a B cell marker assay, the subject is determined to be one or more of: i) a candidate to receive treatment with an anti-VLA-4 therapy, such as natalizumab; ii) not a candidate to receive treatment with an anti-VLA-4 therapy, such as natalizumab; iii) a candidate to receive treatment with an immunomodulator, iv) not a candidate to receive treatment with an immunomodulator; iv) a candidate who should have enhanced monitoring as compared to a subject who is determined to have a B cell marker expression level above a higher risk threshold level, or a combination thereof. For example, a candidate who is determined to have a B cell marker expression level above a higher risk threshold level can be selected as a candidate to receive anti-VLA-4 therapy. In some embodiments, a candidate who has received prior treatment with an anti-VLA-4 therapy, e.g., for more than 1, 2, 3, 4, 5, 6, 7, 8, 9, 10, 11, 12, 13, 14, 15, 16, 17, 18, 19, 20, 21, 22, 23, 24 or more months, and who is determined to have a B cell marker expression level above a higher risk threshold level can be selected as a candidate to receive further anti-VLA-4 therapy. In some embodiments, a candidate who has received prior therapy with an immunosuppressant, and who is determined to have a B cell marker expression level above a higher risk threshold level can be selected as a candidate to receive further anti-VLA-4 therapy. In some embodiments, a candidate who is determined to be JCV positive, but who is determined to have a B cell marker expression level above a higher risk threshold level can be selected as a candidate to receive further anti-VLA-4 therapy. In some embodiments, a subject can be selected as a candidate to receive further anti-VLA-4 therapy, but with a recommendation to monitor the patient more frequently for the development of adverse symptoms, such as symptoms that may indicate the development of PML Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
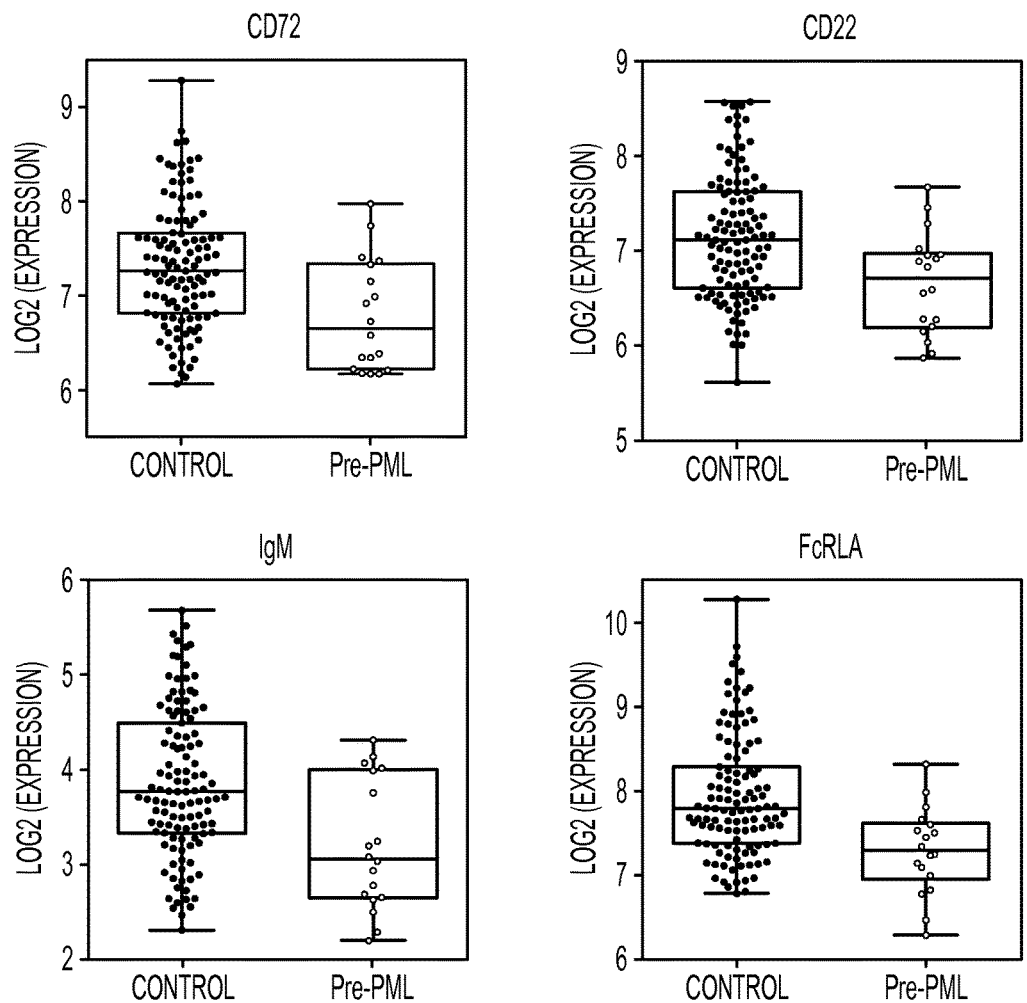
FIG. 1 depicts examples of differentially expressed transcripts in PML versus non-PML patients.

The invention is based, at least in part, on the discovery of new and improved methods of assessing the risk of a patient for PML that include assessing the modulation, e.g., increase or decrease, of various cell markers. The invention is based at least in part on the discovery that the presence or absence and/or amount of one or more B cell specific markers can be an indicator of a patient's risk of developing Progressive Multifocal Leukoencephalopathy (PML).

Applicants have discovered that in patients who have lower expression levels of one or more B cell markers, e.g., one or more B cell marker described herein (e.g., one or more of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b), e.g., as compared to a reference standard, the patient may be at higher risk of developing PML. Applicants have also discovered that in patients who have higher expression levels of one or more B cell makers, e.g., one or more B cell marker described herein (e.g., one or more of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b), e.g., as compared to a reference standard, the patient may be at a lower risk of developing PML. In some embodiment, expression levels of one or more B cell markers alone can be an indicator of a patient's risk of developing PML. In some embodiments, the patient is further evaluated for other parameters associated with a risk of developing PML, including but not limited to, whether the patient has received prior immunosuppressant (IS) therapy, and/or anti-JCV titer.

B cell marker levels may be determined by any available methods. For example, exemplary transcription and translation product detection methods are disclosed herein.

A patient can be monitored at regular intervals, such as every 1 month, 2 months, 3 months, 4 months, 5 months, 6 months, 7 months, 8 months, 9 months, 10 months, 11 months, every 12 months, or more for a change in B cell marker expression levels. A patient can be monitored over a period of time, such as over a period of 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, or more. If the results of a later assay indicate that the patient still has an anti-JCV antibody titer of nOD less than 0.5, and optionally a percent inhibition of <70%, then the patient can be determined to still be at a lower risk for developing PML. If a later assay indicates that the patient's antibody titer is increased by 2 to 3 fold from the initial assay, then the patient can be determined to be at increased or higher risk for developing PML. Applicants observed patients diagnosed with PML tend to demonstrate an increase in antibody titer and nOD by 2 to 3 fold in the six months prior to diagnosis. Furthermore, Applicants observed that patients who have more than one anti-JCV antibody positive sample over time, but the antibody index is consistently below threshold, can be determined to be at lower risk for developing PML. In some embodiments, a patient is at lower risk if the patient is consistently negative for anti-JCV antibodies over a period of time. In some embodiments, a patient is at lower risk if the patient has more than one sample taken over a period of time that is positive for anti-JCV antibodies, where the index level is 1.5 or less. In some embodiments, a patient is at lower risk if the patient has more than one sample taken over a period of time that is positive for anti-JCV antibodies, where the index level is 1.2 or less. In some embodiments, a patient is at lower risk if the patient has more than one sample taken over a period of time that is positive for anti-JCV antibodies, where the index level is 0.9 or less.

A patient has a higher risk of PML if, (i) the anti-JCV antibody titer as indicated by index value or nOD is determined to be >3 and the percent inhibition value is determined to be >70%, or (ii) the patient showed an increase in index, nOD or titer by 2-fold from a previous test. In some embodiments, a patient has a higher risk of PML if the patient is consistently positive for anti-JCV antibodies over a period of time, with an index level above a threshold value, e.g., with an index value of greater than 0.9, greater than 1.0, greater than 1.1, greater than 1.2, greater than 1.3, greater than 1.4, or greater than 1.5. In some embodiments, a patient has a high risk of PML if the patient has more two or more, e.g., 2, 3, 4, 5, 6, or more, consecutive samples over a period of time with an index level above a threshold value, e.g., with an index value of greater than 0.9, greater than 1.0, greater than 1.1, greater than 1.2, greater than 1.3, greater than 1.4, or greater than 1.5.

A patient satisfying these criteria can, optionally, be determined not to be a candidate to receive therapy with an anti-VLA-4 therapy, such as an anti-VLA-4 antibody, e.g., natalizumab, or the patient can further be assessed for other risk factors of developing PML. These risk factors include whether or not the patient has previously received an anti-VLA-4 therapy, such as natalizumab, and for how long the patient has received the therapy; and whether and for how long the patient has previously received an immunosuppressant therapy other than an anti-VLA-4 therapy. A patient's risk of PML may be a combination of each of these factors.

Antibody titer can be measured by "nOD" or "index." "nOD" is the normalized optical density value in a test, such as an ELISA test, for anti-JCV antibody detection. The "index" value is the optical density value for the sample divided by the optical density of the positive control in an immunoassay, such as the ELISA assay.

Applicants previously discovered that patients who received an anti-VLA-4 therapy, such as natalizumab, for 24 months or less, and who have not previously received an immunosuppressant therapy, are at lower risk for developing PML, than patients who do not meet these two criteria. Further, patients who have the lowest risk are those who meet these two criteria, and who are also JCV negative, e.g., patients who do not test positive for anti-JCV antibodies or JCV nucleic acid, e.g., JCV DNA. It was previously unknown that each of these three risk factors ((i) the amount of time the patient has previously received an anti-VLA-4 therapy; (ii) whether or not a patient has previously received treatment with an immunosuppressant other than an anti-VLA-4 therapy; and (iii) JCV status) independently contribute to a patient's risk of PML. The inventions described herein can be used in general for patients treated with a VLA-4 inhibitor. The ability to identify subpopulations of patients at distinctly different PML risks allows for better characterization of risk than previous methods (i.e., overall PML risk) and should assist healthcare professionals and patients in making more informed benefit-risk treatment decisions. These risk assessment criteria are described in co-owned U.S. provisional applications 61/491,810, filed May 31, 2011, and 61/508584, filed Jul. 15, 2011. The contents of each of these provisional applications is hereby incorporated by reference in its entirety. The risk criteria described herein directed to anti-JCV antibody titer (e.g., as measured by nOD or index level) and, optionally percent inhibition can be considered in combination with the risk factors described in the prior co-owned provisional applications.

The methods for determining PML risk can require acquiring one, two or all three of a JCV classification for a patient (e.g., anti-JCV antibody titer, such as measured by nOD or index level and, optionally percent inhibition), prior anti-VLA-4 therapy history for the patient, and prior immunosuppressant therapy history (other than anti-VLA-4 therapy) for the patient. Responsive to these classifications, a patient can be assigned a treatment suitability classification. Patients who are determined to have low risk of developing PML can be assigned a positive treatment classification, and patients who are determined to have a higher relative risk of developing PML can be assigned a negative treatment classification. A patient who receives a positive treatment classification can receive a recommendation for further treatment or for initiating treatment with an anti-VLA-4 therapy. A patient receiving a negative treatment classification may receive a recommendation to terminate treatment with an anti-VLA-4, a recommendation to initiate treatment with a non-anti-VLA-4 therapy, a recommendation for continuing or initiating anti-VLA4 therapy with increased surveillance for signs and symptoms of PML.

A recommendation for further treatment with an anti-VLA-4 therapy may be accompanied with further instructions or requirements that the patient receive additional or enhanced monitoring, such as if one or more factors indicate that the patient may be at an increased risk of PML, e.g., prior treatment with an anti-VLA-4 therapy for longer than 24 months, e.g., 25 months or longer, or prior treatment with an immunosuppressant other than an anti-VLA-4 therapy.

A patient can be determined to have previously received an anti-VLA-4 therapy or an immunosuppressant therapy other than an anti-VLA-4 therapy through self-reporting by the patient, or through information (verbal or written) provided by a parent, physician, physician's assistant, nurse or other healthcare provider. The information can also be obtained through a database, such as a medical database or a clinical trials database.

Prior immunosuppressant therapies, other than anti-VLA-4 therapy, that will be indicative of an increased risk of PML can include prior treatment with antineoplastics, immunosuppressants or immunomodulators, such as one or more beta-interferon or glatiramer acetate. Exemplary immunosuppressants include, e.g., mitoxantrone, methotrexate, azathioprine, cyclophosphamide, and mycophenolate, anti-CD20 therapy (e.g., rituximab), an anti-CD11a therapy (e.g., efalizumab), or mycophenolate mofetil. Prior treatment with other immunosuppressant therapies as described below will also be predicted to increase a patient's risk of PML following further administration of an anti-VLA-4 therapy. In general, a determination of prior immunosuppressant use is a specified use which can be any prior use of an immunosuppressant that is not a VLA-4 inhibitor (e.g., an anti-VLA-4 antibody) (e.g., in the patient's lifetime) or prior use within a specified period of time, for example, within the previous 1, 2, 3, 5, or 10 years prior to the evaluation of PML risk.

If the presence of a B cell marker is identified in a biological sample from a patient, e.g., one or more B cell marker, e.g., one or more B cell marker described herein (e.g., one or more of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b proteins, peptides, or nucleic acids, the patient is determined to be "B cell marker positive." A positive B cell marker classification corresponds to the presence of the one or more B cell markers in the biological sample, e.g., one or more B cell marker expression levels that are equal to or greater than a preselected criterion. The preselected criterion is typically a qualitative value, e.g., a "detectable" amount of protein, peptide or nucleic acid according to a particular assay, e.g., an immunoassay.

The methods described herein for determining PML risk can be useful for any human subject, including a subject considering treatment with an immunomodulator, for example an anti-VLA-4 therapy (e.g., natalizumab), an anti-CD20 therapy (e.g., rituximab), an anti-CD11a therapy (e.g., efalizumab), or mycophenolate mofetil; in a subject currently being treated with an immunomodulator; or a subject that has ceased treatment with an immunomodulator. The method may be useful to others who may be susceptible to PML such as individuals having lymphoproliferative disorders, such as multiple myeloma or a lymphoma; individuals infected with human immunodeficiency virus (HIV), or having acquired immune deficiency syndrome (AIDS), hematologic malignancies, or an autoimmune disease such as systemic lupus erythematosus (SLE), an inflammatory bowel disease, such as Crohn's Disease (CD) or ulcerative colitis, multiple sclerosis (MS) or arthritis, e.g., rheumatoid arthritis (RA). The risk-assessment method may also be useful to subjects receiving immunosuppressive or immunomodulatory therapies, such as transplant patients. Exemplary immunosuppressive or immunomodulatory therapies include natalizumab, rituximab, efalizumab, and mycophenolate mofetil. The method can be useful for assessing risk in a subject having a disorder, or being treated with a drug, disclosed in Piccinni et al. "Stronger association of drug-induced progressive multifocal leukoencephalopathy (PML) with biological immunomodulating agents" *Eur. J. Clin. Pharmacol.* 66:199-206, 2010, the contents of which are incorporated herein by reference.

Definitions

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a physical process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non covalent bond, between a first and a second atom of the analyte; or by changing the structure of a reagent, or a fragment or other derivative thereof, e.g., by breaking or forming a covalent or non covalent bond, between a first and a second atom of the reagent.

"Acquiring a sample" as the term is used herein, refers to obtaining possession of a sample, e.g., a tissue sample or protein sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a protein sample or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

As used herein, the term "probe" refers to any molecule which is capable of selectively binding to a specifically intended target molecule, for example, a transcription product, e.g., an mRNA or cDNA, or a translation product, e.g., a polypeptide or protein. Probes can be either synthesized by one skilled in the art, or derived from appropriate biological preparations. For purposes of detection of the target molecule, probes can be specifically designed to be labeled, as described herein. Examples of molecules that can be utilized as probes include, but are not limited to, RNA, DNA, proteins, antibodies, and organic monomers.

"Sample," "tissue sample," "subject or patient sample," "subject or patient cell or tissue sample" or "specimen" each refers to a biological sample obtained from a tissue, e.g., a bodily fluid, of a subject or patient. The source of the tissue sample can be solid tissue as from a fresh, frozen and/or preserved organ, tissue sample, biopsy, or aspirate; blood or any blood constituents (e.g., serum, plasma); bodily fluids such as cerebral spinal fluid, whole blood, plasma and serum. The sample can include a non-cellular fraction (e.g., plasma, serum, or other non-cellular body fluid). In one embodiment, the sample is a serum sample. In other embodiments, the body fluid from which the sample is obtained from an individual comprises blood (e.g., whole blood). In certain embodiments, the blood can be further processed to obtain plasma or serum. In another embodiment, the sample contains a tissue, cells (e.g., peripheral blood mononuclear cells (PBMC)). In an embodiment the sample includes B cells. For example, the sample can be a fine needle biopsy sample, an archival sample (e.g., an archived sample with a known diagnosis and/or treatment history), a histological section (e.g., a frozen or formalin-fixed section, e.g., after long term storage), among others. The term sample includes any material obtained and/or derived from a biological sample, including a polypeptide, and nucleic acid (e.g., genomic DNA, cDNA, RNA) purified or processed from the sample. Purification and/or processing of the sample can involve one or more of extraction, concentration, antibody isolation, sorting, concentration, fixation, addition of reagents and the like. The sample can contain compounds that are not naturally intermixed with the tissue in nature such as preservatives, anticoagulants, buffers, fixatives, nutrients, antibiotics or the like.

Probes and Methods for Detection of Translation Products

Probe-based methods for detection of translation products include, but are not limited to: Western blot, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF) mass spectrometry, microcytometry, microarray, microscopy, fluorescence activated cell sorting (FACS), flow cytometry, laser scanning cytometry, hematology analyzer and assays based on a property of the protein including but not limited to DNA binding, ligand binding, or interaction with other protein partners.

The translation product or polypeptide can be detected and quantified by any of a number of means well known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry and the like. A skilled artisan can readily adapt known protein/antibody detection methods for use in determining the expression level of one or more biomarkers in a serum sample.

A useful probe for detecting a polypeptide is an antibody capable of binding to the polypeptide, e.g., an antibody with a detectable label. Antibodies can be polyclonal or monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

An antibody probe can be labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair {e.g., biotin-streptavidin}), or an antibody fragment (e.g., a single-chain antibody, an isolated antibody hypervariable domain, etc.) which binds specifically with a protein corresponding to the marker, such as the protein encoded by the open reading frame corresponding to the marker or such a protein which has undergone all or a portion of its normal post-translational modification, is used.

Immunohistochemistry or IHC refers to the process of localizing antigens (e.g. proteins), e.g., in cells of a tissue section or other sample, exploiting the principle of antibodies binding specifically to antigens in biological tissues. Specific molecular markers are characteristic of particular cellular events such as proliferation or cell death (apoptosis). Visualizing an antibody-antigen interaction can be accomplished in a number of ways. In the most common instance, an antibody is conjugated to an enzyme, such as peroxidase, that can catalyze a color-producing reaction. Alternatively, the antibody can also be tagged to a fluorophore, such as fluorescein, rhodamine, DyLight Fluor or Alexa Fluor.

Proteins from tissue samples, e.g., cells, can be isolated using techniques that are well known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

In one format, antibodies, or antibody fragments, can be used as probes in methods such as Western blots or immunofluorescence techniques to detect the expressed proteins. In such uses, one can immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know other suitable carriers for binding antibody or antigen, and will be able to adapt such support for use with the present invention. For example, protein isolated from cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means. Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

In another embodiment, Western blot (immunoblot) analysis is used to detect and quantify the presence of a polypeptide in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind a polypeptide. The anti-polypeptide antibodies specifically bind to the polypeptide on the solid support. These antibodies can be directly labeled or alternatively can be subsequently detected using labeled antibodies (e.g., labeled sheep anti-human antibodies) that specifically bind to the anti-polypeptide.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The polypeptide is detected and/or quantified using any of a number of well recognized immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology,* Academic Press, Inc. New York; Stites & Terr (1991) *Basic and Clinical Immunology* 7th Edition.

In another embodiment, the polypeptide is detected and/or quantified using Luminex™ assay technology. The Luminex™ assay separates tiny color-coded beads into e.g., distinct sets that are each coated with a reagent for a particular bioassay, allowing the capture and detection of specific analytes from a sample in a multiplex manner. The Luminex™ assay technology can be compared to a multiplex ELISA assay using bead-based fluorescence cytometry to detect analytes such as biomarkers.

In another embodiment, the polypeptide is detected and/or quantified using isoelectric focusing (IEF). IEF technology separates molecules, e.g., proteins, based on differences in their isoelectric point (pI), e.g., which generally correlates with the relative content of acidic and basic residues in the protein. Proteins can be separated by isoelectric focusing as a first step in two-dimensional gel electrophoresis, and may be further separated based on molecular weight, e.g., through SDS-PAGE.

Immunological binding assays (or immunoassays) typically utilize a "capture agent" to specifically bind to and often immobilize the analyte (polypeptide or subsequence). The capture agent is a moiety that specifically binds to the analyte. In another embodiment, the capture agent is an antibody that specifically binds a polypeptide. The antibody (anti-peptide) can be produced by any of a number of means well known to those of skill in the art.

Immunoassays also often utilize a labeling agent to specifically bind to and label the binding complex formed by the capture agent and the analyte. The labeling agent can itself be one of the moieties comprising the antibody/analyte complex. Thus, the labeling agent can be a labeled polypeptide or a labeled anti-antibody. Alternatively, the labeling agent can be a third moiety, such as another antibody, that specifically binds to the antibody/polypeptide complex.

In one embodiment, the labeling agent is a second human antibody bearing a label. Alternatively, the second antibody can lack a label, but it can, in turn, be bound by a labeled third antibody specific to antibodies of the species from which the second antibody is derived. The second can be modified with a detectable moiety, e.g., as biotin, to which a third labeled molecule can specifically bind, such as enzyme-labeled streptavidin.

Other proteins capable of specifically binding immunoglobulin constant regions, such as protein A or protein G can also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.,* 111: 1401-1406, and Akerstrom (1985) *J. Immunol.,* 135: 2589-2542).

As indicated above, immunoassays for the detection and/or quantification of a polypeptide can take a wide variety of formats well known to those of skill in the art.

Exemplary immunoassays for detecting a polypeptide can be competitive or noncompetitive. Noncompetitive immunoassays are assays in which the amount of captured analyte is directly measured. In one "sandwich" assay, for example, the capture agent (anti-peptide antibodies) can be bound directly to a solid substrate where they are immobilized. These immobilized antibodies then capture polypeptide present in the test sample. The polypeptide thus immobilized is then bound by a labeling agent, such as a second human antibody bearing a label.

In competitive assays, the amount of analyte (polypeptide) present in the sample is measured indirectly by measuring the amount of an added (exogenous) analyte (polypeptide) displaced (or competed away) from a capture agent (anti-peptide antibody) by the analyte present in the sample. In one competitive assay, a known amount of, in this case, a polypeptide is added to the sample and the sample is then contacted with a capture agent. The amount of polypeptide bound to the antibody is inversely proportional to the concentration of polypeptide present in the sample.

In another embodiment, the antibody is immobilized on a solid substrate. The amount of polypeptide bound to the antibody can be determined either by measuring the amount of polypeptide present in a polypeptide/antibody complex, or alternatively by measuring the amount of remaining uncomplexed polypeptide. The amount of polypeptide can be detected by providing a labeled polypeptide.

The assays described herein are scored (as positive or negative or quantity of polypeptide) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of polypeptide.

In another embodiment, level (activity) is assayed by measuring the enzymatic activity of the gene product. Methods of assaying the activity of an enzyme are well known to those of skill in the art.

In vivo techniques for detection of a marker protein include introducing into a subject a labeled antibody directed against the protein. For example, the antibody can be labeled with a radioactive marker whose presence and location in a subject can be detected by standard imaging techniques.

Certain markers identified by the methods of the invention can be secreted proteins. It is a simple matter for the skilled artisan to determine whether any particular marker protein is a secreted protein. In order to make this determination, the marker protein is expressed in, for example, a mammalian cell, e.g., a human cell line, extracellular fluid is collected, and the presence or absence of the protein in the extracellular fluid is assessed (e.g., using a labeled antibody which binds specifically with the protein).

Antibodies can be used a probes for translation products. The terms "antibody" and "antibody substance" as used interchangeably herein refer to immunoglobulin molecules and immunologically active portions of immunoglobulin molecules, i.e., molecules that contain an antigen binding site which specifically binds an antigen, such as a polypeptide of the invention. A molecule which specifically binds to a given polypeptide is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. Probes can be polyclonal or monoclonal antibodies. The term "monoclonal antibody" or "monoclonal antibody composition", as used herein, refers to a population of antibody molecules that contain only one species of an antigen binding site capable of immunoreacting with a particular epitope.

An antibody directed against a polypeptide can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. The antibodies can also be used diagnostically to monitor protein levels in tissues or body fluids (e.g., in a tumor cell-containing body fluid) as part of a clinical testing procedure, e.g., to, for example, determine the efficacy of a given treatment regimen. Detection can be facilitated by coupling the antibody to a detectable substance. Examples of detectable substances include, but are not limited to, various enzymes, prosthetic groups, fluorescent materials, luminescent materials, bioluminescent materials, and radioactive materials. Examples of suitable enzymes include, but are not limited to, horseradish peroxidase, alkaline phosphatase, β-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin, and examples of suitable radioactive materials include, but are not limited to, $^{125}$I, $^{131}$I, $^{35}$S or $^{3}$H.

Probes and Methods for Detection of Transcription Products

Transcriptional expression can be assessed by any of a wide variety of well known methods for detecting expression. Non-limiting examples of such methods include nucleic acid hybridization methods, nucleic acid reverse transcription methods, and nucleic acid amplification methods.

In certain embodiments, activity of a particular gene is characterized by a measure of gene transcript (e.g., mRNA). Detection can involve quantification of the level of gene expression (e.g., cDNA, mRNA), or, alternatively, can be a qualitative assessment of the level of gene expression, in particular in comparison with a control level. The type of level being detected will be clear from the context.

Methods of detecting and/or quantifying the gene transcript (mRNA or cDNA made therefrom) using nucleic acid hybridization techniques are known to those of skill in the art (see e.g., Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the target cDNA.

A general principle of such diagnostic and prognostic assays involves preparing a sample or reaction mixture that can contain a marker, and a probe, under appropriate conditions and for a time sufficient to allow the marker and probe to interact and bind, thus forming a complex that can be removed and/or detected in the reaction mixture. These assays can be conducted in a variety of ways.

For example, one method to conduct such an assay would involve anchoring the marker or probe onto a solid phase support, also referred to as a substrate, and detecting target marker/probe complexes anchored on the solid phase at the end of the reaction. In one embodiment of such a method, a sample from a subject, which is to be assayed for presence and/or concentration of marker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, marker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the marker or probe belongs. Well-known supports or carriers include, but are not limited to, glass, polystyrene, nylon, polypropylene, polyethylene, dextran, amylases, natural and modified celluloses, polyacrylamides, gabbros, and magnetite.

In order to conduct assays with the above-mentioned approaches, the non-immobilized component is added to the solid phase upon which the second component is anchored. After the reaction is complete, uncomplexed components can be removed (e.g., by washing) under conditions such that any complexes formed will remain immobilized upon the solid phase. The detection of marker/probe complexes anchored to the solid phase can be accomplished in a number of methods outlined herein.

In another embodiment, the probe, when it is the unanchored assay component, can be labeled for the purpose of detection and readout of the assay, either directly or indirectly, with detectable labels discussed herein and which are well-known to one skilled in the art.

It is also possible to directly detect marker/probe complex formation without further manipulation or labeling of either component (marker or probe), for example by utilizing the technique of fluorescence energy transfer (see, for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a marker can be accomplished without labeling either assay component (probe or marker) by utilizing a technology such as real-time Biomolecular Interaction Analysis (BIA) (see, e.g., Sjolander, S. and Urbaniczky, C., 1991, *Anal. Chem.* 63:2338-2345 and Szabo et al., 1995, *Curr. Opin. Struct. Biol.* 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with marker and probe as solutes in a liquid phase. In such an assay, the complexed marker and probe are separated from uncomplexed components by any of a number of standard techniques, including but not limited to: differential centrifugation, chromatography, electrophoresis and immunoprecipitation. In differential centrifugation, marker/probe complexes can be separated from uncomplexed assay components through a series of centrifugal steps, due to the different sedimentation equilibria of complexes based on their different sizes and densities (see, for example, Rivas, G., and Minton, A. P., 1993, *Trends Biochem Sci.* 18(8):284-7). Standard chromatographic techniques can also be utilized to separate complexed molecules from uncomplexed ones. For example, gel filtration chromatography separates molecules based on size, and through the utilization of an appropriate gel filtration resin in a column format, for example, the relatively larger complex can be separated from the relatively smaller uncomplexed components. Similarly, the relatively different charge properties of the marker/probe complex as compared to the uncomplexed components can be exploited to differentiate the complex from uncomplexed components, for example, through the utilization of ion-exchange chromatography resins. Such resins and chromatographic techniques are well known to one skilled in the art (see, e.g., Heegaard, N. H., 1998, *J. Mol. Recognit.* Winter 11(1-6):141-8; Hage, D. S., and Tweed, S. A. *J Chromatogr B Biomed Sci Appl* 1997 Oct. 10; 699(1-2):499-525). Gel electrophoresis can also be employed to separate complexed assay components from unbound components (see, e.g., Ausubel et al., ed., *Current Protocols in Molecular Biology,* John Wiley & Sons, New York 1987-1999). In this technique, protein or nucleic acid complexes are separated based on size or charge, for example. In order to maintain the binding interaction during the electrophoretic process, non-denaturing gel matrix materials and conditions in the absence of reducing agent are typical. Appropriate conditions to the particular assay and components thereof will be well known to one skilled in the art.

In a particular embodiment, the level of mRNA corresponding to the marker can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from cells (see, e.g., Ausubel et al., ed., *Current Protocols in Molecular Biology,* John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated nucleic acid can be used in hybridization or amplification assays that include, but are not limited to, Southern or Northern analyses, polymerase chain reaction analyses and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a marker of the present invention. Other suitable probes for use in the diagnostic assays of the invention are described herein. Hybridization of an mRNA with the probe indicates that the marker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the markers of the present invention.

The probes can be full length or less than the full length of the nucleic acid sequence encoding the protein. Shorter probes are empirically tested for specificity. Exemplary nucleic acid probes are 20 bases or longer in length (See, e.g., Sambrook et al. for methods of selecting nucleic acid probe sequences for use in nucleic acid hybridization). Visualization of the hybridized portions allows the qualitative determination of the presence or absence of cDNA.

An alternative method for determining the level of a transcript involves the process of nucleic acid amplification, e.g., by rtPCR (the experimental embodiment set forth in Mullis, 1987, U.S. Pat. No. 4,683,202), ligase chain reaction (Barany, 1991, *Proc. Natl. Acad. Sci. USA,* 88:189-193), self sustained sequence replication (Guatelli et al., 1990, *Proc. Natl. Acad. Sci. USA* 87:1874-1878), transcriptional amplification system (Kwoh et al., 1989, *Proc. Natl. Acad. Sci. USA* 86:1173-1177), Q-Beta Replicase (Lizardi et al., 1988, *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. Fluorogenic rtPCR can also be used in the methods of the invention. In fluorogenic rtPCR, quantitation is based on amount of fluorescence signals, e.g., TaqMan and sybr green. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the cells prior to detection. In such methods, a cell or tissue sample is prepared/processed using known histological methods. The sample is then immobilized on a support, typically a glass slide, and then contacted with a probe that can hybridize to mRNA that encodes the marker.

As an alternative to making determinations based on the absolute expression level of the marker, determinations can be based on the normalized expression level of the marker. Expression levels are normalized by correcting the absolute expression level of a marker by comparing its expression to the expression of a gene that is not a marker, e.g., a housekeeping gene that is constitutively expressed. Suitable genes for normalization include housekeeping genes such as the actin gene, or epithelial cell-specific genes. This normalization allows the comparison of the expression level in one sample, e.g., a subject sample, to another sample, e.g., a healthy subject, or between samples from different sources.

Alternatively, the expression level can be provided as a relative expression level. To determine a relative expression level of a marker, the level of expression of the marker is determined for 10 or more samples of normal versus PML isolates, or even 50 or more samples, prior to the determination of the expression level for the sample in question. The mean expression level of each of the genes assayed in the larger number of samples is determined and this is used as a baseline expression level for the marker. The expression level of the marker determined for the test sample (absolute level of expression) is then divided by the mean expression value obtained for that marker. This provides a relative expression level.

In certain embodiments, the samples used in the baseline determination will be from samples derived from a subject having PML versus samples from a healthy subject of the same tissue type. The choice of the cell source is dependent on the use of the relative expression level. Using expression found in normal tissues as a mean expression score aids in validating whether the marker assayed is specific to the tissue from which the cell was derived (versus normal cells). In addition, as more data is accumulated, the mean expression value can be revised, providing improved relative expression values based on accumulated data. Expression data from normal cells provides a means for grading the risk of PML.

In another embodiment, expression of a marker is assessed by preparing mRNA/cDNA (i.e., a transcribed polynucleotide) from cells in a subject sample, and by hybridizing the genomic DNA or mRNA/cDNA with a reference polynucleotide which is a complement of a polynucleotide comprising the marker, and fragments thereof. cDNA can, optionally, be amplified using any of a variety of polymerase chain reaction methods prior to hybridization with the reference polynucleotide. Expression of one or more markers can likewise be detected using quantitative PCR (QPCR) to assess the level of expression of the marker(s). Alternatively, any of the many known methods of detecting mutations or variants (e.g., single nucleotide polymorphisms, deletions, etc.) of a marker of the invention can be used to detect occurrence of a mutated marker in a subject.

In a related embodiment, a mixture of transcribed polynucleotides obtained from the sample is contacted with a substrate having fixed thereto a polynucleotide complementary to or homologous with at least a portion (e.g., at least 7, at least 10, at least 15, at least 20, at least 25, at least 30, at least 40, at least 50, at least 100, at least 500, or more nucleotide residues) of a marker of the invention. If polynucleotides complementary to or homologous with a marker of the invention are differentially detectable on the substrate (e.g., detectable using different chromophores or fluorophores, or fixed to different selected positions), then the levels of expression of a plurality of markers can be assessed simultaneously using a single substrate (e.g., a "gene chip" microarray of polynucleotides fixed at selected positions). When a method of assessing marker expression is used which involves hybridization of one nucleic acid with another, the hybridization can be performed under stringent hybridization conditions.

In another embodiment, a combination of methods to assess the expression of a marker is utilized.

Because the compositions, kits, and methods of the invention rely on detection of a difference in expression levels of one or more markers of the invention, in certain embodiments the level of expression of the marker is significantly greater than the minimum detection limit of the method used to assess expression in at least one of a biological sample from a subject with PML, at risk for PML, or a healthy control.

A nucleic acid molecule of the invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the invention can be prepared by standard synthetic techniques, e.g., using an automated DNA synthesizer.

Probes based on the sequence of a nucleic acid molecule of the invention can be used to detect transcripts (e.g., mRNA) or genomic sequences corresponding to one or more markers of the invention. The probe comprises a label group attached thereto, e.g., a radioisotope, a fluorescent compound, an enzyme, or an enzyme co-factor. Such probes can be used as part of a diagnostic test kit for identifying cells or tissues which mis-express the protein, such as by measuring levels of a nucleic acid molecule encoding the protein in a sample of cells from a subject, e.g., detecting mRNA levels or determining whether a gene encoding the protein has been mutated or deleted.

The methods described herein can also include molecular beacon nucleic acid molecules having at least one region which is complementary to a nucleic acid molecule of the invention, such that the molecular beacon is useful for quantitating the presence of the nucleic acid molecule of the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

"Under conditions effective to permit complex formation" generally means conditions in which the reagents have been diluted to reduce background and provide readouts of results that lie within a specified range. Diluents can include, in non-limiting examples, solutions that include BSA, phosphate buffered saline (PBS), or PBS containing Tween.

"Suitable" conditions also include conditions that are at a temperature and/or for a period of time sufficient to allow effective binding. Incubations are typically from about one to two hours or one to four hours, at temperatures of approximately 25° C. to 27° C., or may be overnight at about 4° C. However, those in the art will understand that other conditions may be suitable.

In general, one or more washes are conducted between the incubations of the assay. Appropriate wash solutions include diluent buffer (e.g., PBS or PBS/Tween) or borate buffer.

A reference sample can be of the same biological material (e.g., blood, plasma, serum, urine, or CSF) isolated from an individual. In some embodiments, the individual is known to be PML positive. In some embodiments, the individual is known to be PML negative. In some embodiments, the individual is known to be untreated with an anti-VLA-4 therapy, e.g., natalizumab. In some embodiments, the individual is known to be JCV negative. In some embodiments, the individual is known to be JCV positive. In some embodiments, the individual is known to be untreated with prior immunosuppressant therapy. In some embodiments, the individual is known to have been treated with prior immunosuppressant therapy.

In one embodiment, the assay is performed in a medical office, such as by a healthcare provider, e.g., a doctor, a nurse or a technician, working in a facility where the biological sample is obtained from a patient. In another embodiment, the biological sample obtained from a patient is transported to another facility, e.g., to a third party facility, where the assay is performed. In this latter case, the results of the assay can be reported back to the healthcare provider, such as through a form, which can be submitted by mail or electronically (e.g., through facsimile or e-mail) or through an on-line database. In one embodiment, the results of the assay (including the screening assay and, optionally, a confirmatory assay) can be stored in a database and can be accessed by a healthcare provider, such as through the worldwide web.

Methods of Evaluating Samples and/or Subjects

As used herein, methods of evaluating or analyzing a subject or biological sample from a subject include one or more of performing the analysis of the sample, requesting analysis of the sample, requesting results from analysis of the sample, or receiving the results from analysis of the sample. (Generally herein, determination (or determining), analysis or evaluation (or evaluating) can include one or both of performing the underlying method or receiving data from another who has performed the underlying method.)

The analysis or evaluation requires a transformation of material, e.g., biological material or assay components. For example, a biological sample (e.g., whole blood, serum or plasma) can be evaluated for the presence of one or more B cell markers, e.g., one or more B cell markers described herein (e.g., one or more of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b). The evaluation can be performed before or after or at the same time the patient is receiving treatment, such as for MS. The evaluation is based, at least in part, on analysis of a sample from the subject, e.g., a blood, plasma, serum, sample. In one embodiment, the sample includes a non-cellular fraction (e.g., plasma, serum, or other non-cellular body fluid). In one embodiment, the sample is a serum sample. In other embodiments, the biological sample obtained from a patient comprises blood (e.g., whole blood). In certain embodiments, the blood can be further processed to obtain plasma or serum.

The presence of one or more B cell markers can be determined by contact with a specific binding agent, e.g., a B cell marker binding agent (e.g., a binding agent described herein, e.g., by a method described herein.

In one embodiment, the sample is analyzed for the level of B cell marker nucleic acid present in the sample, e.g., by a method described herein. For example, nucleic acids can be isolated from the sample and used for PCR amplification or a Next-Generation (Nex-Gen) Sequencing technique. In one embodiment, a crude lysate of the biological sample is subject to an amplification method, such as PCR, and the amplified product is analyzed by one or more of electrophoresis, restriction fragment mapping, hybridization or sequencing to identify whether B cell marker DNA or RNA is present in the sample and how much is in the sample.

The biological sample can be removed from the patient and analyzed.

In some embodiments, the patient sample, e.g., a serum or plasma or whole blood sample or CSF, can be stored prior to testing for the presence of one or more B cell markers, e.g., for B cell marker protein or nucleic acid. The patient sample, e.g., the patient sample containing B cell marker protein or nucleic acid, can be stored for 1-21 days, e.g., 1-14 days or 1-7 days or longer (e.g., one day, two days, three days, five days, seven days, ten days, 14 days, 21 days or longer); for one to six weeks, e.g., one to three weeks or one to two weeks or longer (e.g., up to one week, up to two weeks, up to three weeks, up to six weeks, or longer); or for one to six months, e.g., one to three months or one to two months or longer (e.g., up to one month, up to two months, up to three months, up to six months or longer). The sample can be stored, for example, frozen (e.g., at −80° C. to −20° C.), at 2-8° C., at ambient temperature (18° C-25° C.) or warmer, e.g., at 37° C.

As used herein, the term "acquire" or "acquiring" refers to obtaining possession of a physical entity, or a value, e.g., a numerical value, by "directly acquiring" or "indirectly acquiring" the physical entity or value, e.g., the status of a patient, such as prior exposure to anti-VLA-4 therapy or other immunosuppressants, JVC status, or B cell marker expression status. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non covalent bond, between a first and a second atom of the analyte; or by changing the structure of a reagent, or a fragment or other derivative thereof, e.g., by breaking or forming a covalent or non covalent bond, between a first and a second atom of the reagent.

At least one or both of determining a patient's status (e.g., B cell marker status), or an activity level, and determining if the status has a preselected relationship with a reference standard, includes one or more of analyzing a sample, requesting analysis of the sample, requesting results from analysis of the sample, or receiving the results from analysis of the sample. (Generally, analysis can include one or both of performing the underlying method (e.g., an immunoassay) or receiving data from another who has performed the underlying method.)

VLA-4 is expressed on various leukocytes, including certain populations of B cells and their precursors. VLA-4 plays a role in adhesion of progenitor B cells to bone marrow stromal cells, and is important for the maturation from progenitor B cells into precursor cells (Ryan D H et al. J Clin Invest 88(3):995 1991. VLA-4 has also been shown to be important for activation of human memory B cells (Silvy et al. Eur J Immunol 27(11):2757 1997). In some embodiments, expression level of VLA-4, e.g., VLA-4 protein and/or nucleic acid level, in a sample is determined. In an embodiment, an expression level of VLA-4 in a specific subset of B cells present in a sample is determined. For example, in some embodiments, a VLA-4 expression level is determined in combination with an expression level of one or more B cell markers, e.g., one or more B cell markers disclosed herein.

Anti-VLA-4 Therapy

An anti-VLA-4 therapy is a molecule, e.g., a small molecule compound or protein biologic (e.g., an antibody or fragment thereof, such as an antigen-binding fragment thereof) that blocks VLA-4 activity. The molecule that is the anti-VLA-4 therapy is a VLA-4 antagonist. A VLA-4 antagonist includes any compound that inhibits a VLA-4 integrin from binding a ligand and/or receptor. An anti-VLA-4 therapy can be an antibody (e.g., natalizumab (TYSABRI®)) or fragment thereof, or a soluble form of a ligand. Soluble forms of the ligand proteins for a4 integrins include soluble VCAM-I or fibronectin peptides, VCAM-I fusion proteins, or bifunctional VCAM-I/Ig fusion proteins. For example, a soluble form of a VLA-4 ligand or a fragment thereof may be administered to bind to VLA-4, and in some instances, compete for a VLA-4 binding site on cells, thereby leading to effects similar to the administration of antagonists such as anti-VLA-4 antibodies. For example, soluble VLA-4 integrin mutants that bind VLA-4 ligand but do not elicit integrin-dependent signaling are suitable for use in the described methods. Such mutants can act as competitive inhibitors of wild type integrin protein and are considered "antagonists." Other suitable antagonists are "small molecules."

"Small molecules" are agents that mimic the action of peptides to disrupt VLA-4/ligand interactions by, for instance, binding VLA-4 and blocking interaction with a VLA-4 ligand (e.g., VCAM-I or fibronectin), or by binding a VLA-4 ligand and preventing the ligand from interacting with VLA-4. One exemplary small molecule is an oligosaccharide that mimics the binding domain of a VLA-4 ligand (e.g., fibronectin or VCAM-I) and binds the ligand-binding domain of VLA-4. (See, Devlin et al., *Science* 249: 400-406 (1990); Scott and Smith, *Science* 249:386-390 (1990); and U.S. Pat. No. 4,833,092 (Geysen), all incorporated herein by reference.)

A "small molecule" may be chemical compound, e.g., an organic compound, or a small peptide, or a larger peptide-containing organic compound or non-peptidic organic compound. A "small molecule" is not intended to encompass an antibody or antibody fragment. Although the molecular weight of small molecules is generally less than 2000 Daltons, this figure is not intended as an absolute upper limit on molecular weight.

Combination Therapy or Alternatives to Anti-VLA-4 Therapy

In some embodiments, the anti-VLA-4 therapy, e.g., natalizumab, is administered with a second agent, or an alternative therapy can be administered instead of the anti-VLA-4 therapy, such as when a patient is determined to be at higher risk for PML.

Non-limiting examples of second agents for treating multiple sclerosis in combination with the anti-VLA-4 therapy, or alternative agents for use instead of the anti-VLA-4 therapy, include: fumaric acid salts, such as dimethyl fumarate (e.g., Tecfidera®) or monomethyl fumarate; Sphingosine 1-phosphate (S1P)-antagonists, such as the S1B-blocking antibody Sphingomab; interferons, such as human interferon beta-1a (e.g., AVONEX® or Rebif®)) and interferon β-1b (BETASERON® human interferon β substituted at position 17; Berlex/Chiron); glatiramer acetate (also termed Copolymer 1, Cop-1; COPAXONE® Teva Pharmaceutical Industries, Inc.); an antibody or a fragment thereof (such as an antigen-binding fragment thereof), such as an anti-CD20 antibody, e.g., Rituxan® (rituximab), or an antibody or fragment thereof that competes with or binds an overlapping epitope with rituximab; mixtoxantrone (NOVANTRONE®, Lederle); a chemotherapeutic agent, such as clabribine (LEUSTATIN®), azathioprine (IMURAN®), cyclophosphamide (CYTOXAN®), cyclosporine-A, methotrexate, 4-aminopyridine, and tizanidine; a corticosteroid, such as methylprednisolone (MEDRONE®, Pfizer), or prednisone; CTLA4 Ig; alemtuzumab (MabCAMPATH®) or daclizumab (an antibody that binds CD25); statins; and TNF antagonists.

Glatiramer acetate is a protein formed from a random chain of amino acids (glutamic acid, lysine, alanine and tyrosine (hence GLATiramer)). Glatiramer acetate can be synthesized in solution from these amino acids at a ratio of approximately 5 parts alanine to 3 parts lysine, 1.5 parts glutamic acid and 1 part tyrosine using N-carboxyamino acid anhydrides.

Additional second agents, or agents for use in place of the anti-VLA-4 therapy, include antibodies or antagonists of other human cytokines or growth factors, for example, TNF, LT, IL-1, IL-2, IL-6, IL-7, IL-8, IL-12 IL-15, IL-16, IL-18, EMAP-11, GM-CSF, FGF, and PDGF. Still other exemplary second agents include antibodies to cell surface molecules such as CD2, CD3, CD4, CD8, CD25, CD28, CD30, CD40, CD45, CD69, CD80, CD86, CD90 or their ligands. For example, daclizubmab is an anti-CD25 antibody that may ameliorate multiple sclerosis.

Still other exemplary antibodies include antibodies that provide an activity of an agent described herein, such as an antibody that engages an interferon receptor, e.g., an interferon beta receptor. Typically, in implementations in which the second agent includes an antibody, it binds to a target protein other than VLA-4 or other than an a4 integrin, or at least an epitope on VLA-4 other than one recognized by natalizumab.

Still other additional exemplary second agents include: FK506, rapamycin, mycophenolate mofetil, leflunomide, non-steroidal anti-inflammatory drugs (NSAIDs), for example, phosphodiesterase inhibitors, adenosine agonists, antithrombotic agents, complement inhibitors, adrenergic agents, agents that interfere with signaling by proinflammatory cytokines as described herein, IL-1β converting enzyme inhibitors (e.g., Vx740), anti-P7s, PSGL, TACE inhibitors, T-cell signaling inhibitors such as kinase inhibitors, metalloproteinase inhibitors, sulfasalazine, azathloprine, 6-mercaptopurines, angiotensin converting enzyme inhibitors, soluble cytokine receptors and derivatives thereof, as described herein, anti-inflammatory cytokines (e.g. IL-4, IL-10, IL-13 and TGF).

In some embodiments, a second agent may be used to treat one or more symptoms or side effects of MS. Such agents include, e.g., amantadine, baclofen, papaverine, meclizine, hydroxyzine, sulfamethoxazole, ciprofloxacin, docusate, pemoline, dantrolene, desmopressin, dexamethasone, tolterodine, phenytoin, oxybutynin, bisacodyl, venlafaxine, amitriptyline, methenamine, clonazepam, isoniazid, vardenafil, nitrofurantoin, psyllium hydrophilic mucilloid, alprostadil, gabapentin, nortriptyline, paroxetine, propantheline bromide, modafinil, fluoxetine, phenazopyridine, methylprednisolone, carbamazepine, imipramine, diazepam, sildenafil, bupropion, and sertraline. Many second agents that are small molecules have a molecular weight between 150 and 5000 Daltons.

Examples of TNF antagonists include chimeric, humanized, human or in vitro generated antibodies (or antigen-binding fragments thereof) to TNF (e.g., human TNF α), such as D2E7, (human TNFα antibody, U.S. Pat. No. 6,258,562; BASF), CDP-571/CDP-870/BAY-10-3356 (humanized anti-TNFα antibody; Celltech/Pharmacia), cA2 (chimeric anti-TNFα antibody; REMICADE™, Centocor); anti-TNF antibody fragments (e.g., CPD870); soluble fragments of the TNF receptors, e.g., p55 or p75 human TNF receptors or derivatives thereof, e.g., 75 kd TNFR-IgG (75 kD TNF receptor-IgG fusion protein, ENBREL™; Immunex; see, e.g., *Arthritis & Rheumatism* 37:S295, 1994; *J. Invest. Med.* 44:235A, 1996), p55 kdTNFR-IgG (55 kD TNF receptor-IgG fusion protein (LENERCEPT™)); enzyme antagonists, e.g., TNFα converting enzyme (TACE) inhibitors (e.g., an alpha-sulfonyl hydroxamic acid derivative, WO 01/55112, and N-hydroxyformamide TACE inhibitor GW 3333, -005, or -022); and TNF-bp/s-TNFR (soluble TNF binding protein; see, e.g., *Arthritis & Rheumatism* 39:S284, 1996; *Amer. J. Physiol.-Heart and Circulatory Physiology* 268:37-42, 1995).

In one implementation, the anti-VLA-4 therapy and the second agent are provided as a co-formulation, and the co-formulation is administered to the subject. It is further possible, e.g., at least 24 hours before or after administering the co-formulation, to administer separately one dose of the anti-VLA-4 therapy formulation and then one dose of a formulation containing the second agent. In another implementation, the anti-VLA-4 therapy and the second agent are provided as separate formulations, and the step of administering includes sequentially administering the anti-VLA-4 therapy and the second agent. The sequential administrations can be provided on the same day (e.g., within one hour of one another or at least 3, 6, or 12 hours apart) or on different days.

The anti-VLA-4 therapy and the second agent each can be administered as a plurality of doses separately in time. The anti-VLA-4 therapy and the second agent are typically each administered according to a regimen. The regimen for one or both may have a regular periodicity. The regimen for the anti-VLA-4 therapy can have a different periodicity from the regimen for the second agent, e.g., one can be administered more frequently than the other. In one implementation, one of the anti-VLA-4 therapy and the second agent is administered once weekly and the other once monthly. In another implementation, one of the anti-VLA-4 therapy and the second agent is administered continuously, e.g., over a period of more than 30 minutes but less than 1, 2, 4, or 12 hours, and the other is administered as a bolus. The anti-VLA-4 therapy and the second agent can be administered by any appropriate method, e.g., subcutaneously, intramuscularly, or intravenously.

In some embodiments, each of the anti-VLA-4 therapy and the second agent is administered at the same dose as each is prescribed for monotherapy. In other embodiments, the anti-VLA-4 therapy is administered at a dosage that is equal to or less than an amount required for efficacy if administered alone. Likewise, the second agent can be administered at a dosage that is equal to or less than an amount required for efficacy if administered alone.

Kits

Reagents for performing a B cell marker assay can be provided in the form of a kit. Except for the patient sample, some or all materials required for the assay can be provided in the kit. A kit is any manufacture (e.g., a package or container) comprising at least one reagent, e.g., a probe, e.g., a nucleic acid probe or an antibody, for specifically detecting a translation or transcription product described herein.

The invention encompasses kits having probes for detecting the presence of a polypeptide or nucleic acid in a biological sample, e.g., a sample containing tissue, whole blood, serum, plasma, buccal scrape, saliva, cerebrospinal fluid, urine, stool, and bone marrow. For example, the kit can comprise a labeled compound or agent capable of detecting a polypeptide or an mRNA encoding a polypeptide in a biological sample and means for determining the amount of the polypeptide or mRNA in the sample (e.g., an antibody which binds the polypeptide or an oligonucleotide probe which binds to DNA or mRNA encoding the polypeptide). Kits can also include instructions for interpreting the results obtained using the kit.

A kit can include a plurality of probes for detecting a plurality of translation or transcription products. If a plurality of expression products are to be analyzed the kit can comprise a probe for each.

The kit can comprise one or more probes capable of identifying one or more B cell markers, e.g., one or more B cell marker described herein (e.g., one or more of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b). Suitable probes for a polypeptide include antibodies, antibody derivatives, antibody fragments, and the like. Suitable probes for a transcription product include a nucleic acid include complementary nucleic acids. For example, a kit can include oligonucleotides (labeled or non-labeled) fixed to a substrate, labeled oligonucleotides not bound with a substrate, pairs of PCR primers, molecular beacon probes, and the like.

Kits of the invention can optionally comprise additional components useful for performing the methods of the invention. By way of example, the kit can comprise fluids (e.g., SSC buffer) suitable for annealing complementary nucleic acids or for binding an antibody with a protein with which it specifically binds, one or more sample compartments, an instructional material which describes performance of a method of the invention, a reference sample for comparison of expression levels of the biomarkers described herein, and the like.

A kit can include a device described herein.

For antibody-based kits, the kit can comprise, for example: (1) a first antibody (e.g., attached to a solid support) which binds to a polypeptide corresponding to a marker of the invention; and, optionally, (2) a second, different antibody which binds to either the polypeptide or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a polypeptide corresponding to a marker of the invention or (2) a pair of primers useful for amplifying a nucleic acid molecule corresponding to a marker of the invention. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

A kit can include for example, a substrate, such as a plate with wells coated with an agent capable of binding to one or more B cell markers, e.g., one or more B cell markers described herein (e.g., one or more of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b). The plate can be for example a 6-well plate, a 12-well plate, a 24-well plate, a 48-well plate, a 96-well plate or a 384 well plate. The plates provided in a kit can be pre-coated with an agent capable of binding to one or more B cell markers. In one embodiment the kit includes materials and reagents for use with high-throughput systems such as SPR (Solid Phase Receptacle) tips for use with bioMerieux systems. The kit can also include a protein or nucleic acid corresponding to one or more B cell markers, a substrate capable of binding to one or more B cell markers, e.g., one or more B cell markers described herein (e.g., one or more of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b). In one embodiment, the kit contains a B cell marker positive control. In one embodiment, the kit contains a B cell marker negative control. Solutions containing proteins, nucleic acids, and samples, e.g., sera, can include a preservative, such as sodium azide, e.g., 0.05%, 0.1%, 1.5%, and 2% sodium azide. In one embodiment, a kit featured in the invention can include one or more reagents for detecting a complex containing B cell markers bound to a detection agent. Reagents for detecting the complex include, for example, a detectable reagent, such as TMB (tetramethylbenzidine), a wash buffer, and a stop reagent.

Reporting of Results

The results of the risk-assessment analysis can be reported, such as to a treatment center, or a healthcare provider, or an insurance provider. In one embodiment, the results of the risk-assessment are stored in a database.

In one embodiment, informational material is provided for performing and interpreting the risk assessment. The informational material can provide guidance as to where to report the results of the assessment, such as to a treatment center or healthcare provider or database provider. The informational material can be provided in a kit or a packet, and can include forms for reporting the results of the assessment, including level of one or more B cell markers, e.g., one or more B cell markers disclosed herein, and address and contact information regarding where to send such forms or other related information; or a URL (Uniform Resource Locator) address for reporting the results in an online database or an online application (e.g., an "app"). In another embodiment, the informational material can include guidance regarding whether a patient should receive treatment with an anti-VLA-4 therapy, depending on the patient's risk of PML according to the results of the risk assessment.

The kit or packet may also include instructions and items for the collection or transport of a patient sample to a healthcare provider, or for receiving a sample from a healthcare provider, or for performing the evaluative methods described herein. For example, besides instructional information, a kit or packet featured in the invention can include one or more of a swab or scraper, or a vessel (e.g., a cup, a test tube, an ampoule, or a bag) for collecting, and storing and transporting a biological sample. The kit or packet may also contain supplies for performing an immunoassay or a sequencing assay for detection of B cell marker proteins or nucleic acids, respectively.

A kit can include one or more containers for the reagents required for an assay, e.g., a B cell marker-detection assay. The reagents can be provided in a concentration suitable for use in the assay or with instructions for dilution for use in the assay. In some embodiments, the kit contains separate containers, dividers or compartments for the assay components, and the informational material. For example, the assay components can be contained in a bottle or vial, and the informational material can be contained in a plastic sleeve or packet. In other embodiments, the separate elements of the kit are contained within a single, undivided container. For example, an assay reagent is contained in a bottle or vial that has attached thereto the informational material in the form of a label. In some embodiments, the kit includes a plurality (e.g., a pack) of individual containers, each containing one or more unit forms (e.g., for use with one assay) of an assay component. For example, the kit includes a plurality of ampoules, foil packets, or blister packs, each containing a single unit of assay reagent for use in a screening or confirmatory assay. The containers of the kits can be air tight and/or waterproof. The container can be labeled for use.

The informational material of a kit or packet is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit or packet can obtain substantive information about how to find the information required for the risk assessment analysis, e.g., where and how to identify prior treatments administered to a subject, and how to perform an assay to determine the B cell marker status of a patient. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a plasma, blood or serum sample, and evaluates the sample using an assay described herein, and determines that the sample contains one or more B cell marker proteins or nucleic acids. In some embodiments, the assay provider, e.g., a service provider or healthcare provider, can further determine, e.g., by contacting a healthcare provider or a database service provider, the amount of prior anti-VLA-4 therapy that a patient has received or whether a patient has previously received treatment with an immunomodulator. The assay provider can further determine that the subject is not a candidate to receive treatment with an anti-VLA-4 therapy, such as natalizumab, or that the subject is a candidate to receive treatment with an immunomodulator, or that the subject may be a candidate who should have enhanced monitoring as compared to a subject who is determined to have a positive B cell marker status (e.g., who tests positive for a predetermined level of protein and/or nucleic acid of one or more B cell markers, e.g., one or more B cell markers disclosed herein). For example, a candidate who is determined to be B cell marker positive can be selected as a candidate to receive anti-VLA-4 therapy. In some embodiments, a candidate who has received prior treatment with an anti-VLA-4 therapy, e.g., for more than 1, 2, 3, 4, 5, 6, 7, 8, 9, 10, 11, 12, 13, 14, 15, 16, 17, 18, 19, 20, 21, 22, 23, 24 or more months, and who is determined to be B cell marker positive can be selected as a candidate to receive further anti-VLA-4 therapy. In some embodiments, a candidate who has received prior therapy with an immunosuppressant, and who is determined to be B cell marker positive can be selected as a candidate to receive further anti-VLA-4 therapy. In some embodiments, a candidate who is determined to be JCV positive, but who is determined to be B cell marker positive can be selected as a candidate to receive further anti-VLA-4 therapy. In some embodiments, a subject can be selected as a candidate to receive further anti-VLA-4 therapy, but with a recommendation to monitor the patient more frequently for the development of adverse symptoms, such as symptoms that may indicate the development of PML.

In one embodiment, the assay provider performs an assessment for PML risk as described herein and determines that subject is a candidate to receive treatment with an anti-VLA-4 therapy, such as natalizumab. In one embodiment, the assay provider informs a healthcare provider that the subject is a candidate for treatment with the anti-VLA-4 therapy, and the candidate is administered the anti-VLA-4 therapy. For example, the assay provider may determine that a patient is at a lower risk for PML and subsequently inform the healthcare provider of the determination of the lower risk and that the subject is a candidate for treatment with the anti-VLA-4 therapy.

In another example, the assay provider determines that a patient is at a higher risk for PML and subsequently informs a healthcare provider of the determination of the higher risk, and recommends that the patient is a candidate for treatment with the anti-VLA-4 therapy, but that the patient should undergo increased testing for PML and, optionally, B cell marker status. In one embodiment, the assay provider informs the healthcare provider that the patient is at higher risk of PML and therefore the patient should receive an alternative to anti-VLA-4 therapy, or the patient is a candidate to receive anti-VLA-4 therapy with increased testing for PML and, optionally, B cell marker status.

The assay provider can provide the results of the risk assessment, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

In one embodiment, a healthcare provider or insurance provider or another entity recommends, e.g., to the patient or a second healthcare provider, that a patient undergo a risk assessment for PML as described herein.

PML risk stratification tools are useful as one component in making individual benefit-risk treatment decisions for patients taking or considering taking a VLA4 inhibitor or other therapeutics known to increase risk of developing PML. Quantification of a patient's PML risk can be used, for example, in benefit-risk analysis.

Headings, e.g., (a), (b), (i) etc., are presented merely for ease of reading the specification and claims. The use of headings in the specification or claims does not require the steps or elements be performed in alphabetical or numerical order or the order in which they are presented.

The invention is further illustrated by the following examples, which should not be construed as further limiting.

EXAMPLES

Example 1

B Cell-Specific Signal in Whole Blood and Serum of Natalizumab-Treated PML Patients is Revealed Using Transcript and Protein Profiling Tysabri is a highly efficacious therapy for patients with relapsing multiple sclerosis (MS), however treatment with natalizumab is associated with an increased risk of PML. An understanding of the relative risk of PML is therefore necessary for informed benefit-risk evaluation and treatment decisions. The presence of anti-JCV antibodies in serum, use of immunosuppressants prior to natalizumab treatment and duration of natalizumab treatment are known risk factors for PML development. Additional risk factors may further improve the risk stratification algorithm. PML risk may be associated with intrinsic or induced changes in cellular or/and humoral immune response. In the present example, in order to identify novel blood-based biomarkers of PML risk, we compared global gene expression profiles of whole blood and protein profiles of serum samples between natalizumab-treated PML patients and matched non-PML controls.

Gene Expression Signature for PML Risk

Samples

Whole blood from MS patients taking natalizumab was collected into paxgene tubes and stored at −80 C. until analysis using Affymetrix U133 microarrays. Samples were collected as a part of Biogen Idec clinical trials or in post-marketing setting. We performed the initial experiment using 18 samples from 10 natalizumab PML subjects (8 of the subjects had two time points, all pre-PML diagnosis), and 192 samples from 96 matched controls. To account for random variation in gene expression, we selected two time points 6 month apart subsequent to initiation of natalizumab treatment. All samples from PML patients were collected prior to plasma exchange.

Approach

To identify gene expression differences between MS patients who later developed PML while on natalizumab and those who did not develop PML, we estimated gene expression on the microarrays by linear modeling and measured differences between the two groups by MANOVA. There are 56,000 transcripts on the microarray, so to account for random assay effects and multiple testing, we set up a cut off for gene expression changes of 1.3 fold or greater with p-value of $10^{-4}$ or lower. Differentially expressed genes identified from the microarrays were tested in independent QRTPCR assays on the same set of samples to confirm differential expression. QRTPCR included selected differentially expressed genes based on the microarray profiling, and additional transcripts related to the differentially expressed genes. To confirm the findings, an independent set of 18 samples from 8 PML patients and 114 samples from 54 MS-natalizumab non-PML patients was tested in the QRTPCR assay. As with the first set of samples, this second set included multiple time points for some of the pre-PML patients and two time points for the non-PML subjects. Since only 13 genes were tested in the second samples set, no multiple test corrections were applied, and differential gene expression of 1.3 at p-value <0.05 as significant was considered.

Sample Analysis

RNA Extraction and QC 400 µl of Paxgene preserved blood was arrayed into deep-well plates for automated RNA extraction. RNA extractions were completed on Arrayplex (Beckman Coulter, Indianapolis, Ind.) using Agencourt RNAdvance Blood kit (Part number A35604) according to the manufacturer's specifications. RNA integrity was assessed using the HT RNA reagent kit (Part number 760410, Caliper Life Sciences, Hopkinton, Mass.) using a LabChip GX (PerkinElmer, Waltham, Mass.). RNA samples with a RQS score of >8.0 were considered high quality for downstream microarray processing.

Microarray Sample Labeling, Hybridization and Scanning

Automated sample amplifications and biotin labeling were carried out using the NuGEN Ovation RNA Amplification system V2 (Cat #3100), Ovation WB reagent (Cat #1300) and Encore Biotin module (Cat #4200) (NuGEN Technologies, Inc, San Carlos, Calif.) according to manufacturer's recommendations using an Arrayplex automated liquid handler (Beckman Coulter, Indianapolis, Ind.). 2 ug of biotin labeled sscDNA probe were hybridized to Affymetrix GeneChip HT HG-U133+ PM plate arrays with modified conditions as described in Allaire et al. Washing and staining of the hybridized arrays were completed as described in the GeneChip Expression analysis technical manual for HT plate arrays using the Genechip® Array Station (Affymetrix, Santa Clara, Calif.) with modifications as described in Allaire et al. The processed GeneChip® plate arrays were scanned using GeneTitan scanner (Affymetrix, Santa Clara, Calif.).

QPCR Primer and Probe Design

Real time PCR probe sets were designed using Primer Express 3.0 (Applied Biosystems) using TaqMan MGB Quantification default settings.

RT

Total RNA (1.0-5.0 µg) was reverse transcribed in 20-50 µl using the High Capacity cDNA Reverse Transcription Kit (Applied Biosystems) using random hexamers. The reaction mixture was incubated for 10 min at 25° C., 120 min at 37° C. and finally for 5 min at 85° C., according to instructions from the manufacturer (Applied Biosystems). RT reactions were diluted 5-10-fold prior to qPCR.

High-Throughput qPCR

The 96.96 Dynamic Arrays for the microfluidic Bio-Mark™ system (Fluidigm Corporation, Calif., USA) were used to study gene expression in 6.5 ng cDNA as described below.

Specific Target Amplification

Pre-amplification of cDNA (produced from 25 to 65 ng of total RNA) was performed in the Tetrad thermocycler [at 95° C. for 10 min activation step followed by 14 cycles: 95° C., (15 s), 60° C., (4 min)] in a total volume of 5 µl in the presence of all primers at a concentration of 50 nM. After pre-amplification, 20 µl Low EDTA TE Buffer [10 mM Tris pH8 (Ambion), 0.1 mM EDTA pH8 (Sigma)] was added to each sample.

Sample Mix for BioMark Analysis

The pre-sample mix contained 66.7% 2× Taqman® Gene Expression Master Mix (Applied Biosystems), 6.67% 20× DNA Binding Dye Sample Loading Reagent (Fluidigm), 6.67% 20× EvaGreen™ (Biotium), 20% Low EDTA TE Buffer. Sample mix was obtained by mixing 5.6 µl of the pre-sample mix with 1.9 µl of diluted cDNA.

Assay Mix

A quantity of 3.8 µl 2× Assay Loading Reagent (Fluidigm) and 1.9 µl Low EDTA TE Buffer were mixed with 1.9 µl of primers (20 µM of each forward and reverse primer).

qPCR Conditions

After priming of the 96.96 Dynamic Array in the Nano-Flex™ 4-Integrated Fluidic Circuits (IFC) Controller (Fluidigm), 5 µl of each sample and 5 µl of each assay mix were added to dedicated wells. The dynamic array was then placed again in the IFC Controller for loading and mixing under the following conditions: 50° C. (2 min); 70° C. (30 min) and 25° C. (10 min). The loaded Dynamic Array was transferred to the BioMark™ real-time PCR instrument. After initial incubation at 50° C. (2 min) and activation of the Hotstart enzyme at 95° C. (10 min) cycling was performed using 95° C. (15 s), and 60° C. (1 min) for 35 cycles, followed by melting curve analysis (1° C./3 s).

Data Analysis

Initial data analysis was performed with the Fluidigm real-time PCR analysis software v. 3.0.2 with linear derivative baseline correction and a quality correction set to 0.65.

Analysis of Microarray Data

Raw data in .CEL files were assessed for quality, and analyzed using R (version 2.9) and the Bioconductor LIMMA package (ref: Smyth G K, et al., 2004). Quality control assessment showed that all arrays were of acceptable quality. The arrays were normalized with the Guanine Cytosine Robust Multi-Array Analysis algorithm (GCRMA), which performs a guanine/cytosine-based background-correction, does a quantile normalization between arrays, and summarizes the multiple probes into 1 probe set value using a median polish algorithm (ref: Wu and Irizarry, 2005). Differential gene expression was measured by empirical Bayes t-statistics and p-values were adjusted for false discovery rate correction. Transcripts were also filtered to those considered present in at least 50% in the samples from the same phenotypic group.

Analysis of Fluidigm Data

Fluidigm data was quality controlled and normalized based on the expression levels of the house-keeping genes. The expression level of house-keeping genes across all samples on each plate was graphed using scatter plots with connected lines. The statistics of the house-keeping genes were displayed using box plots. Box plots also drawn for sample well quality and assay quality to filter out any samples and assays with low quality scores. QC plots were drawn and examined for each plate. The variability within and across plates was assessed by the CV vs. Ct plot.

After filtering out the QC failures, we normalized the data using the delta delta method (ref: Livak and Schmittgen, 2001). This method compared the Ct values of the samples of interest with universal human controls (UHCC) as a calibrator. The Ct values of both the calibrator and the samples of interest were normalized to an appropriate endogenous housekeeping gene. The threshold value (CT) records the fractional cycle number at which the fluorescence reaches a fixed threshold (see section 1). Therefore $$X_T = X_0 \times (1+E_X)^{CT,X} = K_X$$

where XT is the threshold number of target molecules, CT; X is the readout CT value, and KX is a constant.

$$-\Delta\Delta C_T = -(\Delta C_{T,q} - \Delta C_{T,ch})$$

The amount of target, normalized to the endogenous reference and relative to a reference sample, is given by:

$$\text{amount of target} = 2^{-\Delta\Delta C_T}$$

Then the normalized delta delta Ct values were analyzed in JMP® 9.0.3 to evaluate any significant change in expression of the genes.

Results

Of the 56,000 transcripts on the affymetrix u133 array, surprisingly fewer than twenty met our differential expression criteria of |fold change |>0.3 and p-value<$10^{-3}$. Several genes that were expressed at lower levels in pre-PML subjects compared to non-PML, including CD22, CD72 and IgHM, are known to be specific to B cells. While the expression level differences were modest (1.5-2.0 fold down-regulation) the differential gene expression was replicated by QRTPCR for six transcripts first in the same set of samples as used for microarrays, and then in an independent set of samples.

Interestingly, all six of the differentially expressed transcripts were downregulated in subjects who went on to develop PML. Several of these transcripts are known to be enriched in naive B cells, suggesting these cells may be deficient or defective in patients who develop PML while taking natalizumab (see Table 1). FIG. 1 depicts examples of differentially expressed transcripts in PML versus non-PML patients.

TABLE 1

Results of whole blood transcript filing.

| Gene Symbol | Gene Description | Set 1: Genome-Wide | | Set 1: Fluidigm qPCR | | Set 2: Fluidgm qPCTR | |
|---|---|---|---|---|---|---|---|
| | | P value | Fold change PML/ non-PML | P value | Fold change PML/ non-PML | P value | Fold change PML/ non-PML |
| IGHM | immunoglobulin heavy constant mu | 5.79E−07 | −1.53 | 1.25E−05 | −1.57 | 8.90E−04 | −1.58 |
| CD22 | CD22 molecule | 2.25E−04 | −1.6 | 4.05E−04 | −1.38 | 3.18E−03 | −1.4 |
| CD72 | CD72 molecule | 4.14E−06 | −1.73 | 4.10E−06 | −1.56 | 1.49E−03 | −1.44 |
| FCRLA | Fc receptor-like A | 5.02E−05 | −1.64 | 3.78E−05 | −1.54 | 3.96E−04 | −1.56 |
| FCRL3 | Fc receptor-like 3 | 1.59E−08 | −1.55 | 2.64E−05 | −1.65 | 4.59E−01 | −1.09 |
| IGHD | immunoglobulin heavy constant delta | n/a | n/a | 2.64E−05 | −1.73 | 1.38E−02 | −1.42 |
| IGKC | immunoglobulin heavy kappa constant | n/a | n/a | 2.37E−02 | −1.57 | 1.84E−03 | −1.46 |
| PARP15 | poly (ADP-ribose) polymerase family, member 15 | 9.61E−04 | −1.51E+00 | 1.57E−04 | −1.41 | 4.16E−01 | −1.07 |
| TRD@ | T cell receptor delta locus | 1.13E−04 | −1.42E+00 | 9.78E−05 | −1.53 | 7.31E−01 | 1.05 |
| IGHA1 | immunoglobulin heavy constant alpha 1 | 5.34E−06 | 1.01E+00 | 8.38E−01 | −1.03 | 5.63E−02 | −1.39 |
| TMEM158 | transmembrane protein 158 (gene/pseudogene) | 9.55E−04 | 1.39E+00 | 1.05E−03 | 1.67 | 8.88E−02 | 1.04 |
| CLEC4D | C-type lectin domain family 4, member D | 3.21E−05 | 1.56E+00 | 3.20E−02 | 1.28 | 5.34E−01 | −1.07 |
| PLSCR1 | phospholipid scramblase 1 | 2.81E−06 | 1.33E+00 | 3.59E−01 | 1.11 | 6.05E−01 | −1.06 |

Serum Protein Expression Signature for PML Risk Samples

Serum samples from natalizumab PML patients and matched non-PML controls were used for protein profiling experiments. For Somascan profiling 82 serum samples from 22 PML patients and 73 serum samples from 24 non-PML patients (controls) were used. Samples were collected at one or more time points, and for the patients with multiple time points, samples were collected both prior to initiation of natalizumab treatment, and at approximately 1, 2, 3 years on treatment. A majority of the patients also had samples collected at PML diagnosis.

For Immunoglobulin (IgG) isotype analysis, 143 serum samples from 63 PML patients and 124 serum samples from 62 non-PML patients were used. Those included samples as described in the protein profiling experiment, and additional cross-sectional samples from 41 patients. All samples came from Biogen Idec clinical trials or from post-marketing setting.

Sample Analysis

Somascan Protein Profiling Analysis

Serum samples (65 uL) were analyzed using the SOMAscan discovery platform (SomaLogic Inc, Boulder, Colo.) that consisted of 1128 SOMAmer™ reagents (SOMAmers). Results were reported in relative florescence units (RFU). Sample data was first normalized to remove hybridization artifacts within a run followed by median normalization to remove other assay biases within the run and finally calibrated to remove assay differences between runs.

Serum Concentration of Ig Isotypes

The assays to quantitate IgG1, IgG2, IgG3, IgG4 and IgM in serum samples were performed by IBT/Viracor Laboratories (Lenexa, Kans.) using the Beckman Coulter IMMAGE® Nephelometry platform and commercially available kits (Binding Sites, UK). The method involves Ig interaction with a specific sheep antiserum to form insoluble complexes, and monitoring light scattering of the suspension which is a function of the concentration of Ig in the test sample. Light scattering ability of the antibody-Ig complexes was enhanced by coating anti-Ig antibodies onto latex particles. Controls and patient materials were pre-diluted by the IMMAGE® instrument prior to analysis. The calibrators and controls prepared from delipidated pooled normal human serum and supplied in stabilized liquid form, were diluted 1:5 and 1:50, respectively according to the directions supplied with the kit. A calibration curve plotted against calibration set points was constructed and IgG4 concentrations in samples were intrapolated from the curve. The method was validated by the IBT/Viracor reference laboratory.

Data Analysis

Differential expression of serum proteins between PML and non-PML samples was first performed at cross-sectional time points. Sample outliers were detected by PCA on log2 transformed protein levels. A linear model was estimated for each protein and significance was computed using a moderated t-statistic. Differential analysis was performed using the R "limma" package.

Longitudinal expression profiles were compared between PML and non-PML patients using a linear mixed effect models where the fixed effects were group and number of Tysabri infusions and the random effect was each patient. The additive effect in the model estimated the overall significance between groups over the entire course of Tysabri treatment and the interaction effect in the model estimated the significance between groups in a dose-dependent manner.

Results

Figure 2:
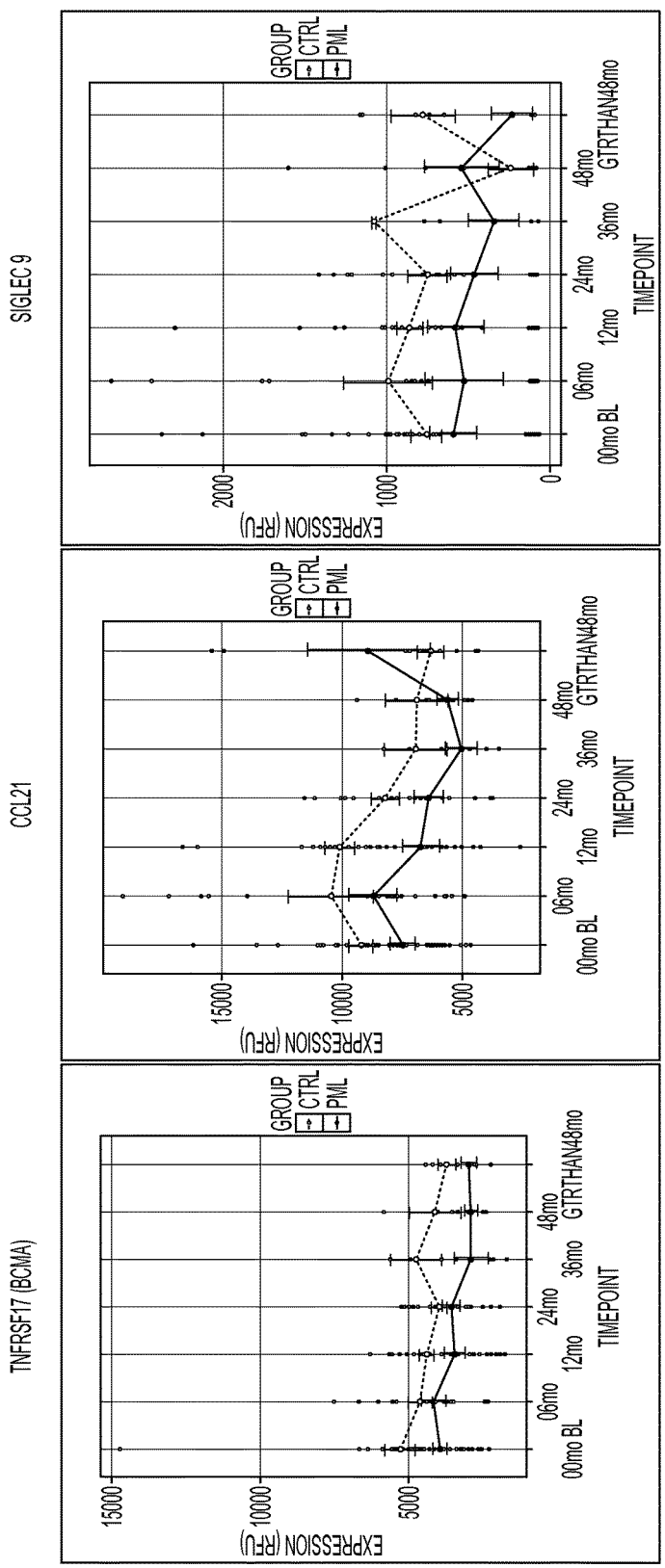
FIG. 2 depicts examples of differentially expressed proteins (BCMA, CCL21, and SIGLEC 9) in PML versus non-PML patients.
Figure 3:
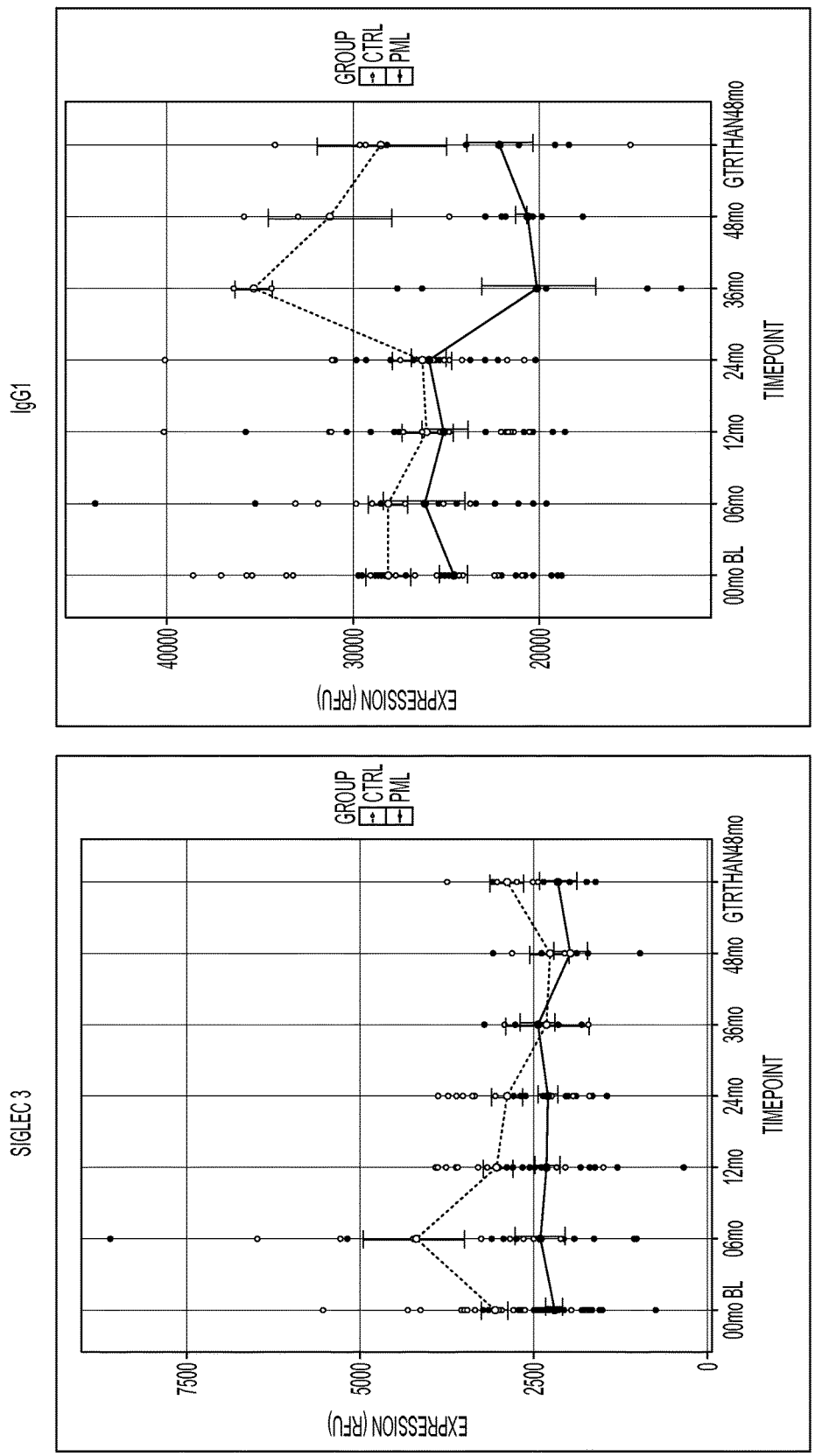
FIG. 3 depicts examples of differentially expressed proteins (SIGLEC 3 and IgG1) in PML versus non-PML patients.
Figure 4:
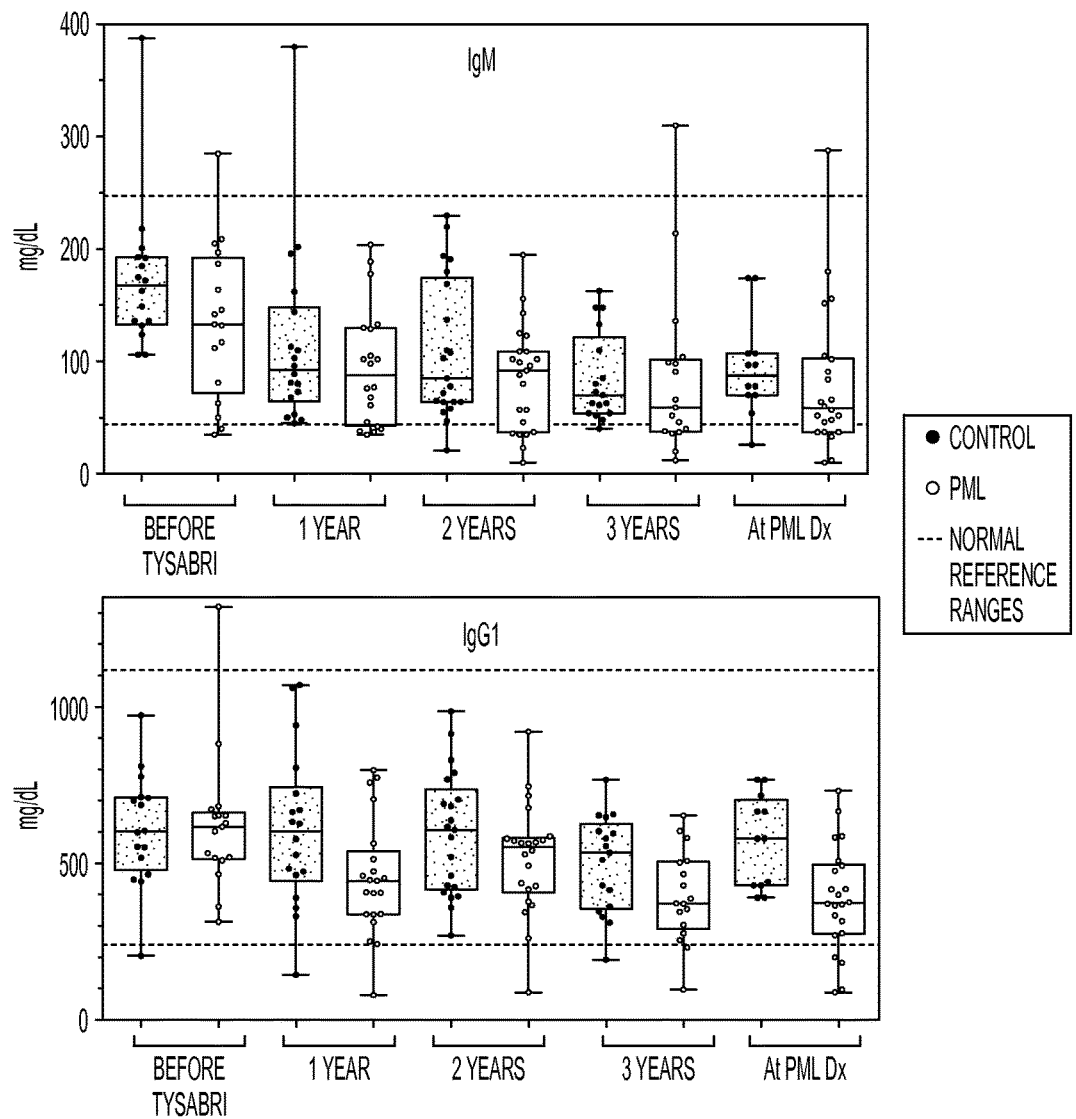
FIG. 4 depicts examples of differentially expressed proteins (IgM and IgG1) in PML versus non-PML patients.

Proteomic profiling of serum using the SomaScan platform revealed a number of proteins that differed in expression between PML and non-PML patients. A majority of the markers were down-regulated in PML patients compared to non-PML controls. Several of the detected down-regulated markers are known to be expressed on B cells or related B cell function (see Table 2). FIGS. 2, 3 and 4 depict examples of differentially expressed proteins.

TABLE 2

Results of serum proteomic Somascan profiling

| Protein | Pre-Tysabri | | 1 year on Tysabri | | 1-2 year before PML | | At PML Diagnosis | |
| --- | --- | --- | --- | --- | --- | --- | --- | --- |
| | P value | Fold change | P value | Fold change | P value | Fold change | P value | Fold change |
| CCL21 | 5.35E−03 | −1.338 | 6.85E−04 | −1.499 | — | — | 1.60E−02 | −1.338 |
| CXCL12 | — | — | — | — | — | — | 5.27E−05 | −1.447 |
| BCMA | 1.46E−02 | −1.380 | 3.56E−02 | −0.302 | — | — | 3.25E−04 | −1.422 |
| IgM | 3.72E−02 | −1.333 | — | — | 2.14E−03 | −2.348 | 1.28E−04 | −2.106 |
| IgG | — | — | — | — | — | — | 1.42E−03 | −1.507 |
| FCGR2A/B | — | — | 1.42E−02 | −1.888 | — | — | — | — |
| SIGLEC-3 | 1.59E−02 | −1.368 | 1.88E−02 | −2.087 | 2.18E−02 | 1.673 | 8.81E−03 | −1.600 |
| SIGLEC-9 | — | — | — | — | — | — | 6.87E−03 | −1.381 |
| IGFBP7 | — | — | — | — | — | — | 2.93E−05 | −0.756 |
| Notch1 | — | — | — | — | — | — | 3.41E−03 | −1.198 |
| Jag1 | — | — | — | — | — | — | 3.65E−03 | −1.413 |
| C3b | — | — | — | — | 2.32E−02 | 2.866 | 2.79E−02 | 2.995 |

Additional serum samples were tested for levels of Ig subclasses using a validated nephelometry-based assay. As a result, it was observed that concentrations of several Ig isotypes tend to be lower in PML patients compared to non-PML controls (Table 3). For example, IgM concentrations measured prior to initiation of Tysabri treatments were lower in PML patients compared to non-PML. Additionally, concentrations of IgG1 seemed to decrease during Tysabri treatment in patients who later developed PML. Overall, patients who developed PML seemed to have IgM and IgG concentrations closer to or below lower normal reference range, suggesting certain degree of immune suppression.

TABLE 3

IgG subclass levels.

| | BL p value | fold change | 6 months p value | fold change | 36 months p value | fold change | 48 months p value | fold change | 48 months+ p value | fold change |
|---|---|---|---|---|---|---|---|---|---|---|
| IgG1 | | | | | | | 1.84E-02 | -0.387 | 1.93E-02 | -0.412 |
| IgG2 | 4.63E-02 | -0.293 | | | 2.73E-02 | -0.479 | | | 3.69E-03 | -0.603 |
| IgG3 | | | 8.37E-03 | -0.955 | | | | | | |
| IgG4 | | | | | | | | | 2.58E-02 | -0.860 |
| IgM | 3.72E-02 | -0.414 | | | | | | | | |

Discussion

Our results reveal that natalizumab patients who develop PML show subtle but reproducible differences in several gene transcripts and proteins compared to patients who do not develop PML. Those differentially expressed transcripts and proteins are enriched in B cell-related markers, specifically naïve B cells, suggesting that changes in B cell compartment of the immune system may play a role in patients' susceptibility to PML.

Extensive transcript and protein profiling of blood also shows that overall transcript and protein markers are relatively stable between PML and non-PML patients, with surprisingly few changes in gene expression and protein levels, including no sign of changes in most immune cell types and no classic antiviral responses in the periphery. Even the differences observed in B cell markers are subtle and may be limited to specific subsets. In the whole genome microarray data, there are no signs of differences in pan-B cell markers such as CD19, but only changes in a very small subset of genes associated with naïve B cells.

Additionally, concentrations of several protein markers including Igs were shown to be lower in PML patients compared to non-PML controls. Those may be used for monitoring patients for changes in immune status that may correlate with risk of developing PML. Interestingly, natalizumab is known to cause an increase in circulating lymphocytes, with most pronounced changes observed for B cells. This may suggest that perturbation in immune cell equilibrium may lead to depletion or functional dis-function of a certain B cell type.

A larger panel of serum samples will be tested for total and JCV-specific Ig isotypes and for other differentially expressed markers, as identified in the profiling experiments. Also, several additional experiments will be performed, such as comprehensive immunophenotyping of peripheral blood cells, BCR and TCR repertoire sequencing, transcript sequencing of peripheral blood cells and assessment of Igs and oligoclonal bands in CSF.

TABLE 4

B Cell Markers.

| | Entrezid | Accession |
|---|---|---|
| Protein | | |
| CCL21 | 6366 | CAG29322 |
| CXCL12 | 6387 | CAG29279 |
| BCMA | 608 | BAB60895 |
| IGM | 3507 | AAC37537 |
| IGG | none | AAA02914 |
| FCGR2A | 2212 | AAH20823 |
| FCGR2B | 2213 | AAI48274 |
| SIGLEC3 | 945 | AAH28152 |
| SIGLEC9 | 27180 | AAQ89272 |
| IGFBP7 | 3490 | NP_001544, NP_001240764 |
| NOTCH1 | 4851 | CAG33502 |
| JAG1 | 182 | AAC51731 |
| C3B | 718 | NP_000055 |
| CXCL13 | 10563 | NP_006410.1 |
| Gene | | |
| IGHM | 3507 | AAC37537.1 |
| IGHD | 3495 | CAA69680.1 |
| IGHK | 50802 | AAH62704.1 |
| FCRLA | 84824 | AAL23899.1 |
| FCRL3 | 115352 | AAH28933.1 |
| CD72 | 971 | NP_001773.1 |
| CD22 | 933 | NP_001762.2 |
| TMEM158 | 25907 | AAH57390.1 |

TABLE 5

Samples from PML Patients from Tysabri Start (54 Pre-PML samples from 22 PML subjects).

| PML Subject ID | BL | 6 mo | 12 mo | 24 mo | 36 mo | 48 mo |
|---|---|---|---|---|---|---|
| 142-101 | x | | x | x | x | |
| 197-119 | x | | x | x | x | |
| 2009BI016462 | | | | | x | |
| 454-110 | x | x | | | | |
| 2009BI018360 | | | | | x | |

TABLE 5-continued

Samples from PML Patients from Tysabri Start (54 Pre-PML samples from 22 PML subjects).

| PML Subject ID | BL | 6 mo | 12 mo | 24 mo | 36 mo | 48 mo |
|---|---|---|---|---|---|---|
| 2009BI018270 | | | x | | | |
| 2009BI027516 | | | x | | | |
| 400-005 | x | | x | x | | |
| 2010BI005566 | | | x | x | x | |
| 2010BI003117 | x | | x | x | | |
| 2010BI025351 | | | x | | | |
| 449-012 | x | | x | x | | |
| 428-005 | x | x | | | | |
| 446-021 | x | | x | | | |
| 429-006 | x | x | | | | |
| 2011BI031122 | x | | x | x | x | |
| 441-007 | x | | x | x | | |
| 661-106 | x | | x | x | | |
| 754-110 | x | | x | x | | |
| 402-006 | x | | x | x | | |
| 454-109 | | | x | x | | |
| 2012BI051723 | | | | | | x |
| Total | 14 | 3 | 16 | 12 | 5 | 2 |

TABLE 6

SOMAlogic Cross-sectional Differential Analysis (BL: Tysabri start)

| Gene | exp2 p value | fold change | BL p value | fold change | 6 months p value | fold change |
|---|---|---|---|---|---|---|
| Siglec-3 (CD33) | 8.81E−03 | −0.678 | 1.59E−02 | −0.452 | 1.88E−02 | −1.062 |
| 6Ckine (CCL21) | 1.60E−02 | −0.420 | 5.35E−03 | −0.351 | | |
| BCMA (TNFRSF17) | 3.25E−04 | −0.508 | 1.46E−02 | −0.464 | | |
| FCG2A/B | | | | | 3.24E−02 | −0.938 |
| MAP2K4 | 4.80E−03 | −0.659 | | | 7.69E−03 | 0.623 |
| IgG | 1.87E−03 | −0.409 | 3.81E−02 | −0.204 | | |
| CD5L | 3.20E−02 | −0.386 | 2.98E−02 | −0.423 | | |
| IL-17 sR (IL17RA) | 2.55E−02 | −0.451 | | | | |
| CK-MB (CKB, CKM) | 5.81E−03 | −0.786 | | | | |
| C3b | 2.79E−02 | 1.583 | | | | |

| Gene | 12 months p value | fold change | 24 months p value | fold change | 36 months p value | fold change |
|---|---|---|---|---|---|---|
| Siglec-3 (CD33) | | | 4.12E−02 | −0.351 | | |
| 6Ckine (CCL21) | 6.85E−04 | −0.584 | | | | |
| BCMA (TNFRSF17) | 3.56E−02 | −0.381 | | | | |
| FCG2A/B | 1.42E−02 | −0.917 | 3.02E−02 | −0.806 | | |
| MAP2K4 | 3.48E−03 | −0.886 | | | | |
| IgG | | | | | 3.62E−02 | −0.886 |
| CD5L | | | | | 4.46E−02 | −0.616 |
| IL-17 sR (IL17RA) | | | 4.74E−02 | −0.424 | 2.88E−02 | −0.854 |
| CK-MB (CKB, CKM) | | | 4.22E−02 | −0.651 | 4.12E−02 | −1.670 |
| C3b | | | 2.32E−02 | 1.519 | 1.34E−02 | 2.625 |

Other embodiments are in the claims.

What is claimed is:

1. A method of treating a patient in need thereof with an immunomodulator, the method comprising:
   determining expression levels of one or more B cell marker in a biological sample from the patient, wherein the one or more B cell marker is selected from the group consisting of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b, and the biological sample is selected from whole blood, serum, or a plasma sample;
   determining whether there is a significant difference in expression levels of the of one or more B cell marker compared to a reference standard, wherein the patient is determined to be at higher risk of developing PML when there is a significant difference and the patient is determined to be at a lower risk of developing PML when the expression levels are the same or substantially similar to the reference standard, thereby evaluating the patient's risk of developing PML; and
   administering the immunomodulator to the patient, wherein administering the immunomodulatory comprises:
   i) administering an anti-VLA-4 therapy to a patient determined to be at lower risk of developing PML;
   ii) administering an anti-VLA-4 therapy and administering increased testing for PML to a patient determined to be at higher risk of developing PML; or
   iii) administering a non anti-VLA-4 therapy to the patient determined to be at higher risk of developing PML,
   wherein the non anti-VLA-4 therapy is selected from the group consisting of interferon beta-1b, interferon beta-1a, dimethyl fumarate, monomethyl fumarate, a sphingosine 1-phosphate antagonist, glatiramer acetate, an antibody therapy, an anti-CD20 antibody, an anti-CD25 antibody, rituximab, a chemotherapeutic agent, mixtoxantrone, a statin, a TNF antagonist, a corticosteroid, clarabine, azathioprine, methotrexate, cyclophosphamide, cyclosporine-A, 4-aminopyridine, tizanidine, methylprednisone, prednisone, CTLA-4 Ig, alemtuzumab, and daclizumab.

2. The method of claim 1, wherein the reference standard is the expression levels of the one or more B cell marker in a patient treated with an anti-VLA4 antibody that does not develop PML.

3. The method of claim 2, wherein the anti-VLA4 antibody is natalizumab.

4. The method of claim 1, further comprising obtaining a biological sample from the patient, and wherein the biological sample comprises a non-cellular fraction, a serum sample, a blood sample, or a blood sample which is further processed to obtain plasma or serum.

5. The method of claim 1, further comprising obtaining a nucleic acid or protein from the sample to determine expression levels of the B cell marker, wherein:
   i) the B cell marker nucleic acid is genomic DNA, cDNA, RNA, or mRNA and the nucleic acid amount is determined using an assay selected from the group consisting of Northern blotting, RT-PCR, and a biochips, and wherein the nucleic acid is mRNA, and
   ii) the B cell marker protein amount is determined using an assay selected from the group consisting of an enzyme linked immunosorbent assay (ELISA), a radioimmunoassay (RIA), a Western blot and an immunohistochemical method.

6. The method of claim 1, wherein IgM protein expression level or IgM nucleic acid expression level is determined.

7. The method of claim 6, wherein the patient is determined to have:
   i) a lower risk of PML if IgM expression levels as determined are above a lower risk expression threshold level of 250 mg/dL,
   ii) a higher risk of PML if IgM levels as determined are below a higher risk expression threshold level of 50 mg/dL, or
   iii) an intermediate risk of PML if the patient has IgM levels between the lower risk expression threshold level of 250 mg/dL and the higher risk expression threshold level of 50 mg/dL), and,
   a patient determined to have an intermediate risk of PML is subjected to further evaluation of risk of PML.

8. The method of claim 7, wherein:
   i) the lower risk nucleic acid threshold level for IgM is above 4 log2,
   ii) the higher risk nucleic acid threshold level of IgM is 3 1og2 or lower, or
   iii) the patient is determined to be at intermediate risk of developing PML if IgM nucleic acid levels are determined to be between 3 log2 and 4.5 log2.

9. The method of claim 6, wherein the patient is identified as at higher risk of developing PML, if there is a 1.2, 1.3, 1.4, 1.5, 1.6, 1.7, 1.8, 1.9, 2 fold or more decrease in IgM protein expression levels or IgM nucleic acid expression levels, as compared to the reference standard.

10. The method of claim 1, wherein:
    i) the patient has not received treatment with an anti-VLA4 antibody at the time of determination, or
    ii) the patient has been receiving administration of the anti-VLA antibody for at least one week, two weeks, one month, 2, 3, 4, 5, 6, 7, 8, 9, 10, 11 months, 1, 2 or 3 years at the time of determination.

11. The method of claim 10, wherein the patient is determined to have:
    i) a lower risk of PML if IgM protein expression levels as determined are above a lower risk expression threshold level of 200 mg/dL,
    ii) a higher risk of PML if IgM protein expression levels as determined are below a higher risk expression threshold level of 100 mg/dL or lower, or
    iii) an intermediate risk of developing PML if IgM protein expression levels are determined to be between 100 and 200 mg/dL.

12. The method of claim 1, wherein IgG1 protein expression level or IgG1 nucleic acid expression level is determined.

13. The method of claim 12, wherein the patient is determined to have:
    i) a lower risk of PML if IgG1 expression levels as determined are above a lower risk expression threshold level,
    ii) a higher risk of PML if IgG1 levels as determined are below a higher risk expression threshold level, or
    iii) an intermediate risk of PML if the patient has IgG1 levels between the lower risk expression threshold level and the higher risk expression threshold level, and,
    a patient determined to have an intermediate risk of PML is subjected to further evaluation of risk of PML.

14. The method of claim 13, wherein:
    i) the lower risk protein expression threshold level of IgG1 is above 1100 mg/dL,
    ii) the higher risk protein expression threshold level of IgG1 is below 240 mg/dL, or
    iii) intermediate risk of developing PML if IgG1 protein levels are determined to be between 240 to 1100 mg/dL.

15. The method of claim 12, wherein the patient has not received treatment with an anti-VLA4 antibody.

16. The method of claim 15, wherein the patient is determined to have:
    i) a lower risk of PML if IgG1 protein expression levels as determined are above a lower risk expression threshold level of 600 mg/dL,
    ii) a higher risk of PML if IgG1 protein expression levels as determined are below a higher risk expression threshold level of 400 mg/dL or lower, or
    iii) an intermediate risk of developing PML if IgG1 protein expression levels are determined to be between 400 and 600 mg/dL.

17. The method of claim 1, wherein the method comprises:
    determining based on the one or more B cell marker expression levels the patient to be at lower risk of developing PML or an intermediate risk of developing PML; and
    administering the anti-VLA-4 therapy to the patient.

18. The method of claim 17, wherein administering the anti-VLA-4 therapy comprises administering an anti-VLA-4 antibody.

19. The method of claim 18, wherein the anti-VLA-4 antibody is natalizumab.

20. The method of claim 1, wherein the method comprises:
    determining based on the one or more B cell marker expression levels the patient to be at higher risk of developing PML or an intermediate risk of developing PML; and
    administering the non anti-VLA-4 therapy to the patient.

21. The method of claim 20, wherein the method comprises stopping administration of anti-VLA-4 therapy and administering the non anti-VLA-4 therapy to the patient.

22. The method of claim 1, wherein the method comprises:
    determining based on the one or more B cell marker expression levels the patient to be at higher risk of developing PML; and
    administering the anti-VLA-4 therapy to the patient with enhanced monitoring for development of PML.

23. A method of treating a patient in need thereof with an immunomodulator, the method comprising:

determining expression levels of one or more B cell marker selected from the group consisting of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b in two or more biological samples, determining whether there is a significant difference in expression levels of the one or more B cell marker compared to a reference standard, wherein the patient is determined to be at higher risk of developing PML when there is a significant difference and the patient is determined to be at a lower risk of developing PML when the expression levels are the same or substantially similar to the reference standard, and wherein the patient is determined to be at an intermediate risk of developing PML when the expression level falls between the lower risk expression threshold level and the higher risk expression threshold level, in a first determination and a second or subsequent determination obtained from the patient over a period of time wherein the patient is administered an anti-VLA4 antibody during at least a portion of the period of time; and the patient's status of being at lower risk, intermediate risk or higher risk of developing PML is evaluated at the time of the determination and is re-evaluated based upon the second or subsequent determination(s); and administering the immunomodulator to the patient, wherein administering the immunomodulatory comprises:
  i) administering an anti-VLA-4 therapy to a patient determined to be at lower risk of developing PML;
  ii) administering an anti-VLA-4 therapy and administering increased testing for PML to a patient determined to be at higher risk of developing PML; or
  iii) administering a non anti-VLA-4 therapy to the patient determined to be at higher risk of developing PML,
wherein the non anti-VLA-4 therapy is selected from the group consisting of interferon beta-1b, interferon beta-1a, dimethyl fumarate, monomethyl fumarate, a sphingosine 1-phosphate antagonist, glatiramer acetate, an antibody therapy, an anti-CD20 antibody, an anti-CD25 antibody, rituximab, a chemotherapeutic agent, mixtoxantrone, a statin, a TNF antagonist, a corticosteroid, clarabine, azathioprine, methotrexate, cyclophosphamide, cyclosporine-A, 4-aminopyridine, tizanidine, methylprednisone, prednisone, CTLA-4 Ig, alemtuzumab, and daclizumab.

24. The method of claim 23, wherein the patient is determined to be at lower risk of developing PML at the time of the initial determination and is re-evaluated to be at higher risk of developing PML based on the second or subsequent determination(s), and the method further comprises:
  administering anti-VLA-4 therapy with enhanced monitoring for development of PML; or
  stopping administration of anti-VLA-4 therapy and administering the non anti-VLA-4 therapy to the patient.

25. The method of claim 24, wherein the anti-VLA-4 therapy comprises an anti-VLA-4 antibody therapy.

26. The method of claim 25, wherein the anti-VLA-4 antibody is natalizumab.

27. A method of treating a patient with an anti-VLA-4 therapy, the method comprising administering to a patient an anti-VLA-4 therapy, wherein the patient has been determined to be at a lower or higher risk of developing PML by a method comprising:
  i) detecting expression levels of one or more B cell marker in a biological sample from the patient, wherein the one or more B cell marker is selected from the group consisting of IGHM, CD22, CD72, FCRLA, FCRL3, IGHD, IGKC, CCL21, CXCL12, BCMA, IgM, IgG, FCGR2A/B, SIGLEC-3, SIGLEC-9, IGFBP7, Notch1, Jag1 and C3b, and the biological sample is selected from whole blood, serum, or a plasma sample;
  ii) determining whether there is a significant difference in expression levels compared to a reference standard, wherein the patient is determined to be at higher risk of developing PML when there is a significant difference and the patient is determined to be at a lower risk of developing PML when the expression levels are the same or substantially similar to the reference standard.

* * * * *